United States Patent [19]

Ogawa et al.

[11] Patent Number: 4,968,786

[45] Date of Patent: Nov. 6, 1990

[54] SIALIC ACID DERIVATIVES, GALACTOSE DERIVATIVES AND METHOD FOR PRODUCING THE SAME

[75] Inventors: Tomoya Ogawa, Musashino; Mamoru Sugimoto, Niiza; Yoshiyasu Shitori, Tokyo; Masayoshi Ito, Kunitachi, all of Japan

[73] Assignees: Rikagaku Kenkyusho, Wako; MECT Corporation, Tokyo, both of Japan

[21] Appl. No.: 749,545

[22] Filed: Jun. 27, 1985

[30] Foreign Application Priority Data

Jun. 28, 1984 [JP] Japan ............... 59-133881
Jun. 28, 1984 [JP] Japan ............... 59-133882

[51] Int. Cl.$^5$ .................... C07H 5/06
[52] U.S. Cl. .................. 536/17.9; 536/17.2; 536/18.4; 536/18.5; 536/123
[58] Field of Search ........... 536/17.9, 17.2, 18.4

[56] References Cited

U.S. PATENT DOCUMENTS

| | | | |
|---|---|---|---|
| 4,348,402 | 9/1982 | Kinast et al. | 536/17.2 |
| 4,495,346 | 1/1985 | Anderson et al. | 536/4.1 |
| 4,514,561 | 4/1985 | Frazer-Reid et al. | 536/4.1 |
| 4,521,240 | 6/1985 | Loh | 536/4.1 |
| 4,521,592 | 6/1985 | Dahmen et al. | 536/4.1 |
| 4,564,675 | 1/1986 | Kunabayashi et al. | 536/4.1 |
| 4,609,478 | 9/1986 | Egan | 536/4.1 |

FOREIGN PATENT DOCUMENTS

| | | | |
|---|---|---|---|
| 0130512 | 10/1979 | Japan | 536/4.1 |
| 0259862 | 12/1969 | U.S.S.R. | 536/4.1 |

OTHER PUBLICATIONS

Journal of Biochemistry, vo. 95, No. 5, 1984, pp. 1323-1329, Handa et al., "Modification of Sialic Acid Carboxyl Group ... ".
Journal of the American Chemical Society, vol. 99, No. 25, 12.7.77, pp. 8279-8282, Czarniecki et al., "Carbon-13 Nuclear Magnetic ... ".
Chemical Abstracts, vol. 77, No. 21, Nov. 20, 1972, p. 484, Ref. No. 140431f, Nakagawa et al., "Structures of Sialooligosaccharides Obtained by Acetolysis of Whale Cartilage ... ".
Carbohydrate Research, vol. 135, No. 2, Jan. 1985, pp. C5-C9; Ogawa et al., "Synthesis of Alpha-Neu5Acrho-(2-3)-D-Gal and ... ".
Biochemical and Biophysical Res. Communications, vol. 132, No. 1, 1985 Oct. 15, 1985, pp. 223-231 Saito et al.: An Acidic Glycosphingolipid, Monosialo-Ganglioside ...
The Jounral of Biological Chemistry, vol. 259, No. 11, Jun. 10, pp. 6818-6825, Bremer et al., Ganglioside-Mediated Modulation of Cell Growth, Growth Factor Binding, and Receptor Phosphorylation.
Hakomori. S., Urdal, D., Yokota, M., & Young, W. W., Jr., "Mass Spectrometric Analysis of Tumor-Associated Glycolipids Antigens with Particular Reference to the Incompatible Blood Group Antigens in Human Cancer", 1980, pp. 3-23.
Migrdichian, *Organic Synthesis* vol. 1, 1957, p. 429.
Lee et al., Chemical Abstracts vol. 91, 1979 p. 720, No. 211756t.
March Advanced Organic Chemistry: Reactions, Mechanisms, and Structure, 1968 p. 664.
Bernstein et al., Chemical Abstracts vol. 97 (1982) No. 145189f.
Lubineau et al., Chemical Abstracts, vol. 84 (1976) No. 105923r.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

Novel sialic acid derivatives and galactose derivatives which are useful intermediate for the synthesis of gangliosides. Methods for the production of the sialic acid and galactose derivatives. Methods for the production of ganglioside $GM_3$.

9 Claims, No Drawings

SIALIC ACID DERIVATIVES, GALACTOSE DERIVATIVES AND METHOD FOR PRODUCING THE SAME

BACKGROUND OF THE INVENTION

This invention relates to sialic acid derivatives and galactose derivatives, more particularly gangliosides and intermediate compounds for use in producing gangliosides, and to methods for producing the same.

Glycolipids found in mammal cells are glycosides between ceramides, which are sphingosines (long chain amino alcohols) to which aliphatic acids have been attached through an amide linkage, and one or more sugars such as glucose, galactose, N-acetyl glucosamine, N-acetyl galactosamine, fucose, sialic acid, etc. Among these glycosides, those containing sialic acid are called gangliosides.

Gangliosides exist mainly in the outer molecular layer of double molecular layers of the mammal cell membrane. Recent studies show that gangliosides play important roles in reception and recognition of, and response to, information in cells, receptor mechanism, differentiation, cell propagation, malignant cell transformation, cell behavior, etc.

However it is very difficult to isolate sialic acid residue-containing oligosaccharides from an organism. Therefore precise synthesis of such sialic acid residue-containing oligosaccharides is necessary for the elucidation of the precise correlation between biological information and the molecular structure of the oligosaccharides.

SUMMARY OF THE INVENTION

An object of this invention is to provide novel gangliosides, novel sialic acid derivatives for use in producing the gangliosides and methods for producing the same.

Another object of this invention is to provide novel galactose and lactose derivatives which can be used as intermediate compounds in producing the gangliosides and methods for producing the same.

The novel sialic acid derivatives of this invention are represented by the formula I.

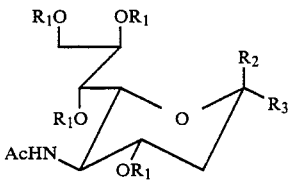

wherein, $R_1$ is hydrogen or acetyl group, one of $R_2$ and $R_3$ is $-COOR_4$ wherein $R_4$ is hydrogen, alkali metal such as sodium and potassium, alkaline earth metal such as calcium or methyl group, the other of $R_2$ and $R_3$ is

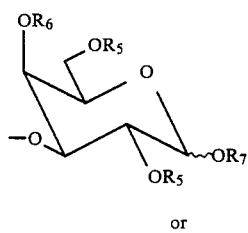

or

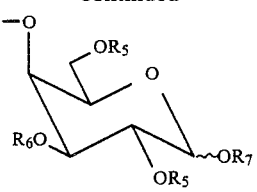

wherein $R_5$ is hydrogen, acetyl or benzyl group, $R_6$ is hydrogen or acetyl group, $R_7$ is hydrogen, acetyl or benzyl group, or

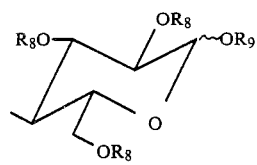

wherein $R_8$ is hydrogen, acetyl or benzyl group, $R_9$ is hydrogen, benzyl, allyl, monochloroacetyl, $-C(CCl_3)=NH$ or

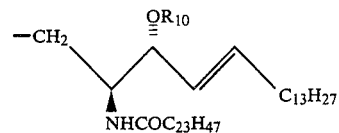

wherein $R_{10}$ is hydrogen or benzoyl group, or $R_2$ and $R_3$ show together

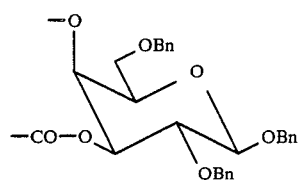

wherein Bn is benzyl group.

The galactose derivatives of this invention are represented by the formula:

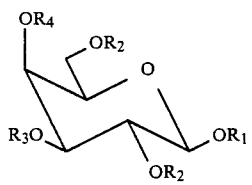

wherein $R_1$ is benzyl group or

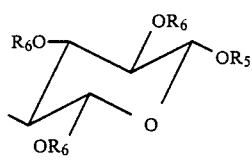

wherein $R_2$ is hydrogen or benzyl group if $R_1$ is benzyl group, otherwise $R_2$ is hydrogen, acetyl or benzyl group, $R_3$ and $R_4$ are hydrogen or form together isopropylidene group, $R_5$ is benzyl or allyl group and $R_6$ is hydrogen, acetyl or benzyl group.

As seen from the above, some of the galactose derivatives provided by this invention are also lactose derivatives.

DETAILED DESCRIPTION OF THE INVENTION

This invention will now be explained in detail.

(a) Synthesis of Ceramide Moiety

Ceramide moieties of gangliosides can be prepared by the method as shown in Scheme 1b. Compound (I) can be prepared by the method as shown in Scheme 1a (see the specification of Japanese Patent Application No. 59-44913).

Compound (ii) is obtained by refluxing overnight an alkyl halide such as 1-bromotetradecane and triphenylphosphine in a solvent such as xylene.

1,2-0-isopropylidene-α-D-xylo-pentodialdo-1,4-furanose (i) is reacted with the compound (ii) in a solvent, e.g. tetrahydrofuran (THF) and hexane in the presence of BuLi to obtain 4-alkylvinyl derivative (iii). The reaction temperature and time are preferably in the range of $-5°$ C. to 25° C. and 0.5 to 24 hours, respectively.

The compound (iii) is treated with methanesulfonylchloride in dry pyridine to obtain 3-methanesulfonyl derivative (iv). The reaction temperature and time are preferably in the range of 0° C. to 25° C. and 2 to 24 hours, respectively.

The compound (iv) is treated in acetic acid - water to remove isopropylidene group. Diol derivative (v) is obtained. The reaction temperature and time are preferably in the range of 70° C. to 90° C. and 0.5 to 5 hours, respectively.

The compound (v) is treated with an oxidizing agent (e.g. sodium metaperiodate) in a solvent (e.g. ethanol) to cleave the diol and then treated with a reducing agent (e.g. sodium borohydride) to obtain diol (vi). The oxidation reaction is preferably conducted at 0° C. to 25° C. for 0.5 to 24 hours. The reduction reaction is preferably conducted at 0° C. to 10° C. for 0.5 to 2 hours.

The compound (vi) is reacted with an alkyl vinyl ether such as ethyl vinyl ether in a solvent such as dichloromethane in the presence of a catalyst such as p-toluenesulfonate to obtain di-alkyl vinyl ether (vii). This reaction is preferably conducted at 0° C. to 30° C. for 0.5 to 24 hours.

The compound (vii) is treated with an azide such as sodium azide in a solvent such as dimethylformamide (DMF) to obtain azide (viii). This reaction is preferably carried out at 70° C. to 120° C. for 8 hours to six days.

The azide (viii) is reduced by a reducing agent such as sodium borohydride and Lindler catalyst/$H_2$ in a solvent such as ethanol and isopropanol to give amine (ix). The reaction is carried out at a reflux temperature for one to six days when sodium borohydride is used and at 0° C. to 30° C. for 2 to 24 hours at a hydrogen pressure of 1 to 4 atms. when Lindler catalyst/$H_2$ is used.

The amine (ix) is reacted with an acyl halide in the presence of an amine such as pyridine and dimethylaminopyridine to obtain amide (x) or (xi). This reaction is preferably carried out at 0° C. to 30° C. for 0.5 to 24 hours. Alternatively, the amine (ix) dissolved in a solvent such as dichloromethane is reacted with an aliphatic acid in the presence of 2-chloro-1-methylpyridinium iodide and tri-n-butylamine to obtain the amide (x) or (xi). This reaction is preferably carried out at a reflux temperature for 0.5 to 13 hours under an inert atmosphere.

The amide (x) or (xi) is treated with pyridinium p-toluenesulfonate, Amberlist A-15 (tradename), etc. in a solvent such as methanol or dichloromethane to obtain ceramide (xii) or (I).

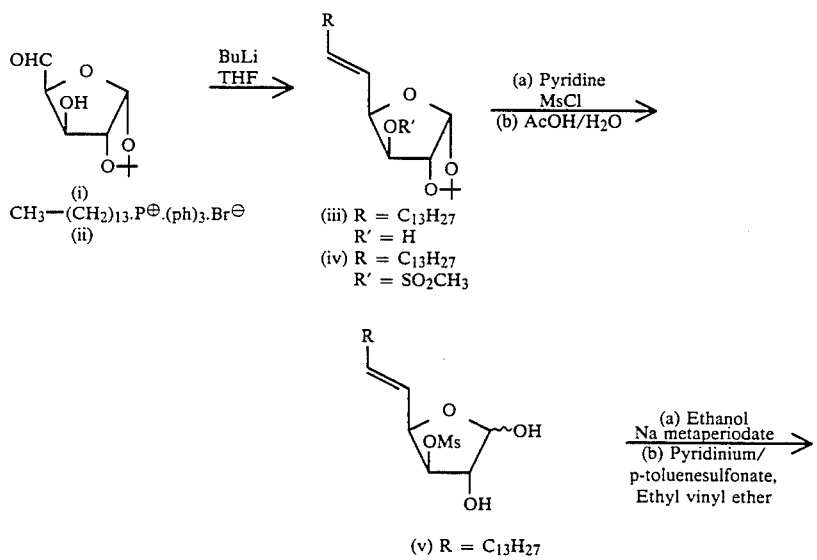

Scheme 1 a

-continued
Scheme 1 a

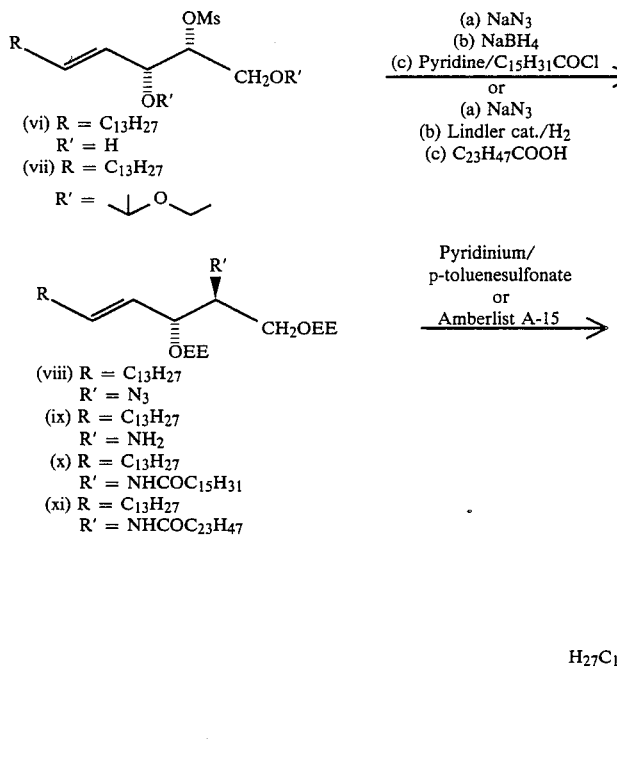

The compound (I) thus obtained is treated with trityl chloride in pyridine to obtain trityl derivative (II) which is then treated with benzoyl chloride and dimethylaminopyridine to obtain trityl - benzoyl derivative (III) which is then treated with p-toluenesulfonic acid to remove the trityl group. Benzoyl ceramide (IV) is obtained. The compound (IV) can be obtained without the isolation of the compounds (II) and (III).

the presence of a catalyst such as tin tetrachloride to obtain allyl derivative (2) which is then deacetylated by a conventional manner, e.g. by NaOMe/MeOH to obtain the deacetylated compound (3) which is further reacted with 2,2-dimethoxypropane and p-toluenesulfonic acid in acetone/DMF. 3', 4'-O-isopropylidene derivative (4) and 4', 6'-O-isopropylidene derivative (5) are obtained. With or without the isolation of the com-

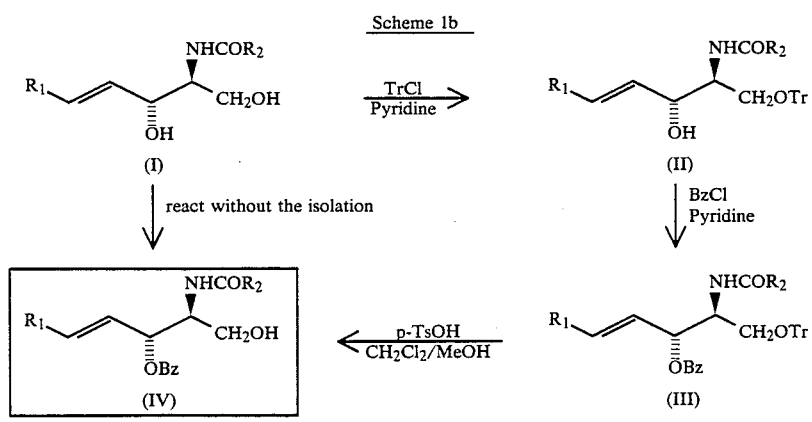

$R_1$: $C_{13}H_{27}$, $R_2$: $C_{23}H_{47}$, Tr: Trityl group, Bz: Benzoyl group (b) Synthesis of Lactose Derivatives and Galactose Derivatives Lactose and galactose derivatives which can be used in producing gangliosides of this invention can be produced by the processes as shown in Schemes 2a and 2b.

D-Lactose octaacetate (1) is treated with tri (n-butyl) tin allyloxide in a solvent such as ethylene chloride in pounds (4) and (5), they are treated with benzyl bromide in DMF in the presence of NaH to obtain penta-O-benzyl derivatives (6) and (7) which are then treated with 90% acetic acid in water to remove isopropylidene group. The compounds (8) and (9) are obtained.

The compound (4) is acetylated by acetic anhydride/pyridine, followed by the treatment with 90% $CF_3COOH$ to obtain the compound (11).

Benzyl 3', 4'-O-isopropylidene lactose (F) is treated in DMF with benzyl bromide in the presence of NaH to obtain benzyl derivative (G) which is then treated with aqueous acetic acid solution to remove isopropylidene group. Hexa-O-benzyl derivative (H) is obtained.

Galactose derivatives which can be used in producing the sialic acid derivatives of this invention can be prepared as follows. Benzyl galactoside (A) suspended in acetone is reacted with 2,2-dimethoxypropane in the presence of p-toluenesulfonic acid to obtain 3,4-0-isopropylidene derivative (B) which is then reacted with benzyl bromide in a solvent, e.g. DMF in the presence of NaH to convert it into tribenzyl derivative (C) which is subsequently treated with aqueous acetic acid solution to remove isopropylidene group. The compound (D) is obtained.

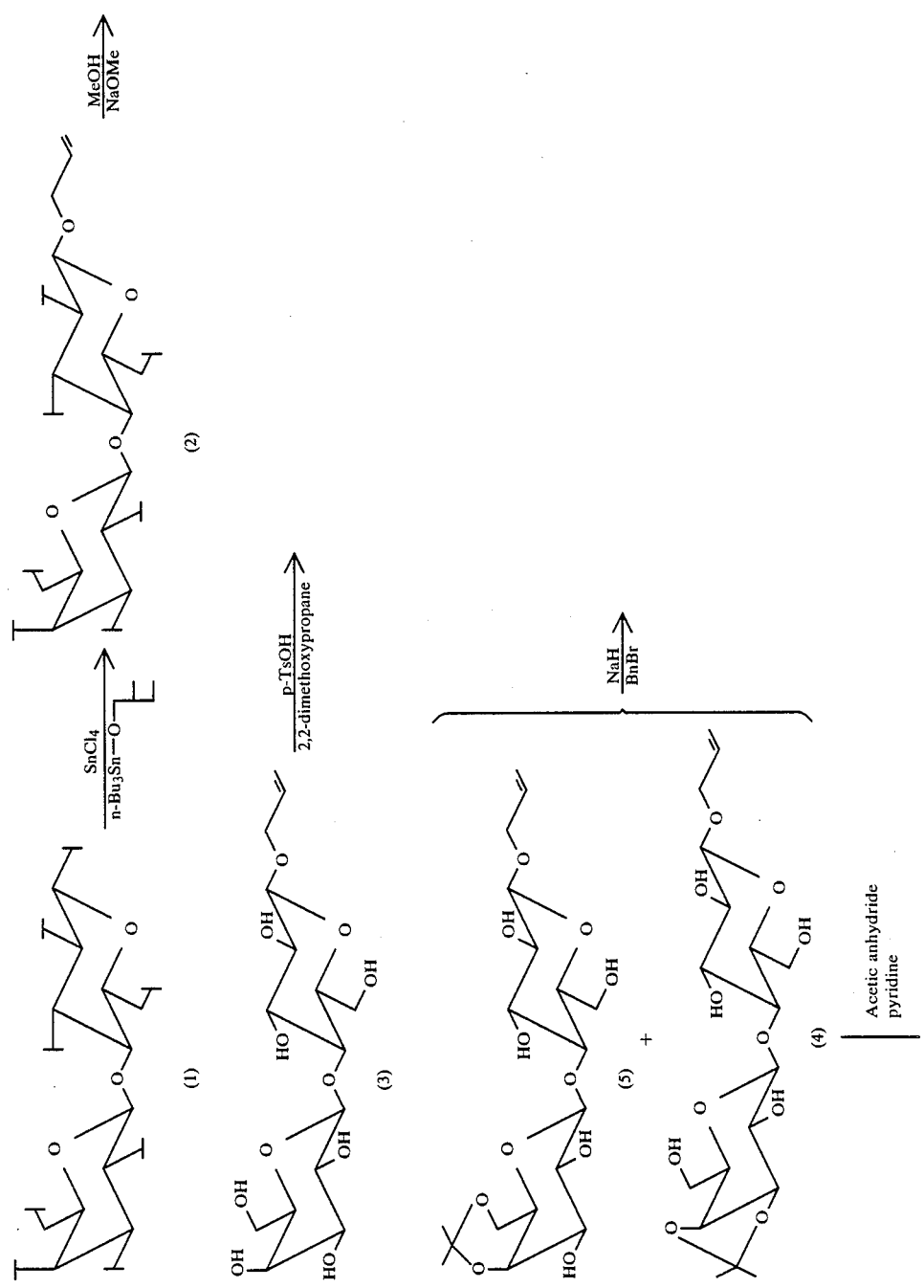

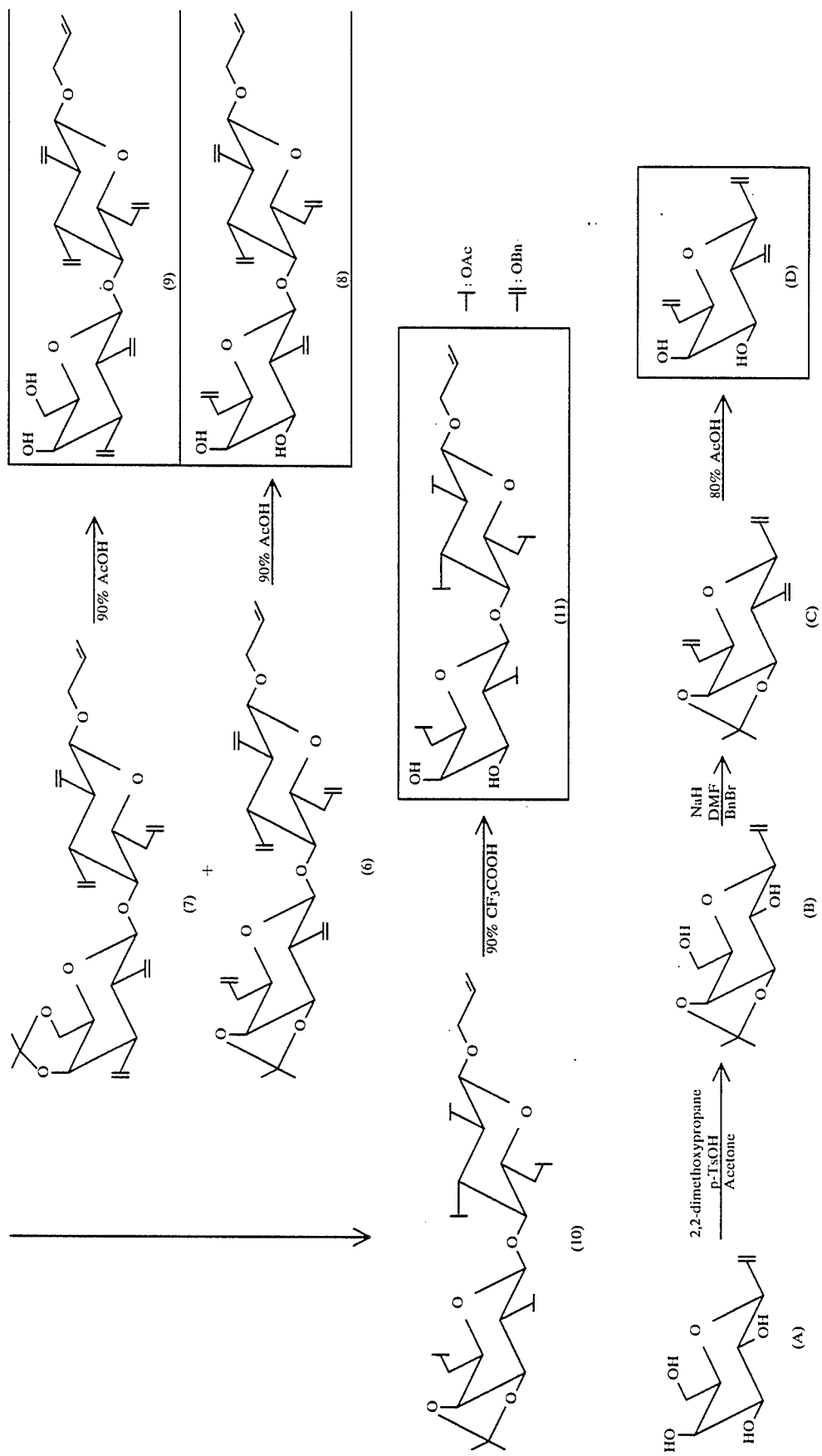

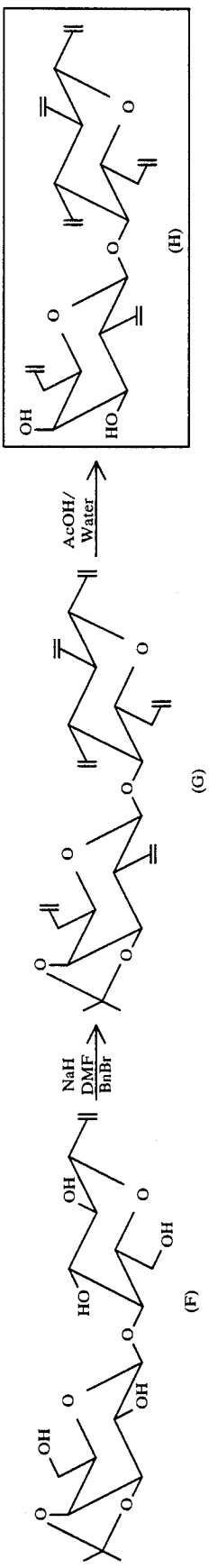

(c) Synthesis of Sialic Acid Derivatives

The compound (8), (9), (11), (D) or (H) is reacted with N-acetyl neuraminic acid acetate methyl ester (E) which can be produced by the Kuhn's method, if necessary, followed by the removal of protective groups, to obtain sialic acid derivatives of this invention.

The reaction between the compound (8), (9), (11), (D) or (H) and the compound (E) is carried out in a solvent such as dichloromethane or 1,2-dichloroethane in the presence of a glycosidation catalyst such as $Hg(CN)_2$, $HgBr_2$, molecular sieve (hereinafter referred to as MS), $Ag_2CO_3$, $AgClO_4$, $AgOSO_2CF_3$, $(CH_3)_3COSO_2CF_3$, etc. at -20° C. to 150° C. for 1 to 120 hours.

Trisaccharide (12), (13), (14), (45), (46) or (47) or disaccharide (31), (32) or (33) is obtained. The removal of protective groups of these compounds gives the desired compounds, respectively. The compound (13) is acetylated by acetic anhydride-pyridine to give the compound (15) which is then treated with $PdCl_2$ and AcONa/AcOH to remove allyl group. The resulting compound (16) is treated with monochloroacetic anhydride-pyridine to obtain the compound (17). Catalytic reduction of the compound (17) and subsequent acetylation give the compound (18) which is then treated sodium acetate and thiourea in a solvent such as ethanol to give the compound (19). Treatment of the compound (19) with trichloroacetonitrile in the presence of NaH in a solvent such as $CH_2Cl_2$ gives the compound (20). This compound is reacted with the ceramide (IV) in the presence of MS4A and $BF_3.Et_2O$ to give the compound (21). Deacetylation and debenzoylation of the compound (21) give the compound (22) or ganglioside $GM_3$.

The compound (23) is treated in a similar manner to give a epimer of ganglioside $GM_3$ (28) (see scheme 5). Alternatively, ganglioside $GM_3$ (the compound (22)) may be produced as follows:

The compound (47) is acetylated by acetic anhydridepyridine to obtain the compound (52). Catalytic reduction of this compound is carried out in a solvent such as MeOH using 10% Pd-C to remove benzyl groups. The resulting debenzylated compound (53) is acetylated by acetic anhydride-pyridine to obtain peracetate (54) which is then treated with hydrazinium acetate in a solvent such as DMF at 30° C. to 80° C. for 5 to 30 minutes to obtain the compound (19) which is subsequently reacted with trichloroacetonitrile in a solvent such as methylene chloride in the presence of NaH under ice-cooled condition. The resulting compound (20) is reacted with the ceramide (IV) under an inert gas atmosphere such as argon in the presence of a glycosidation catalyst such as $BF_3.Et_2O$/molecular sieve 4Å. The compound (21) thus obtained is treated in a conventional manner to remove acetyl and benzoyl groups and neutralized by Amberlist A-15 (tradename) to obtain ganglioside $GM_3$ (22).

Specific examples of the processes of this invention are shown in Schemes 3 to 10 as set below.

Scheme 3

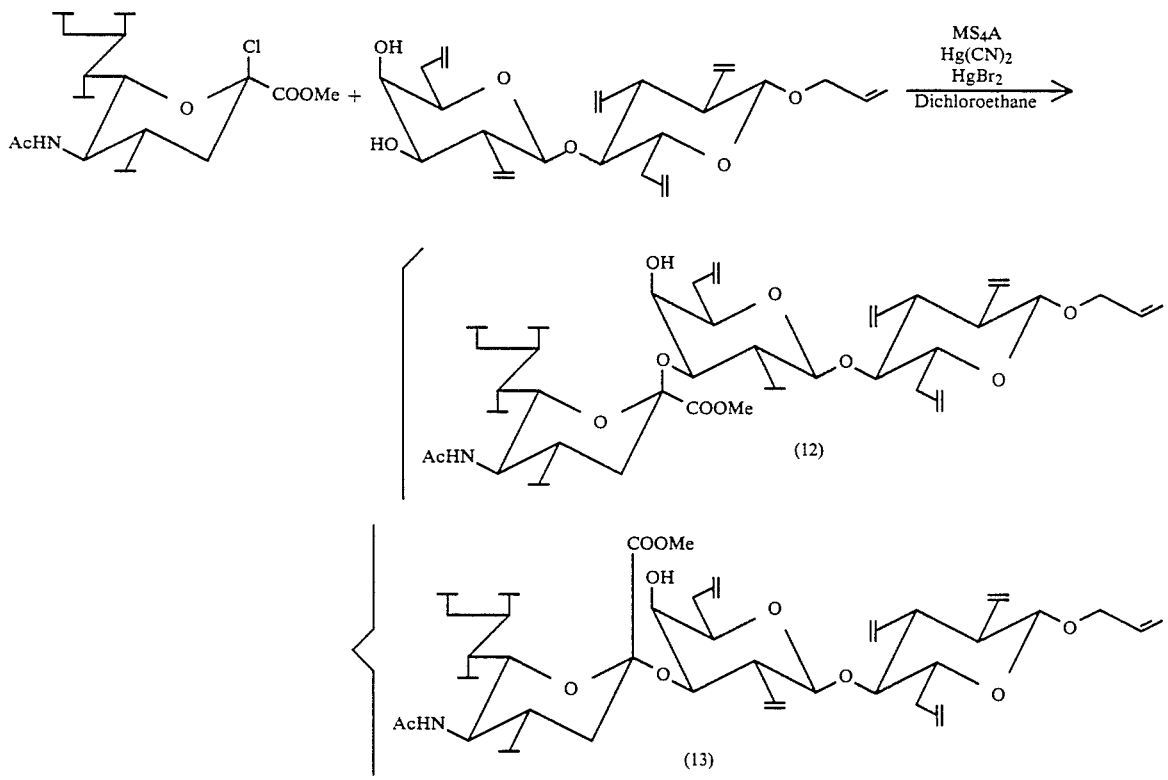

-continued
Scheme 3
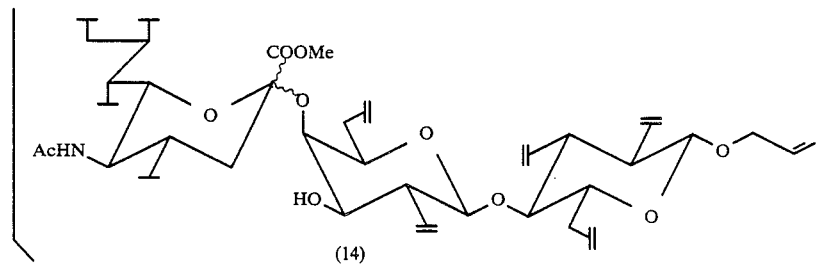
(14)
Scheme 4
(13) →[Pyridine Acetic anhydride]
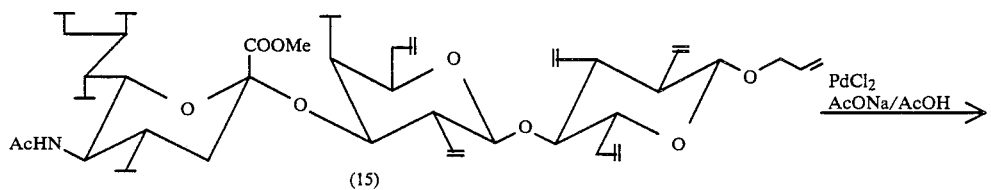
(15) →[PdCl₂ AcONa/AcOH]
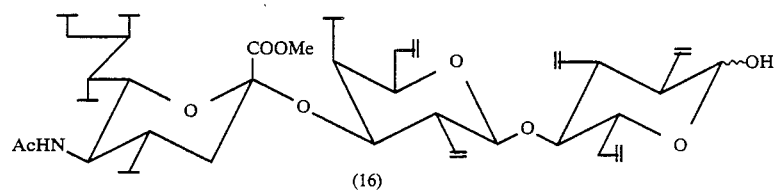
(16)
(16) →[Pyridine Monochloroacetic-anhydride]
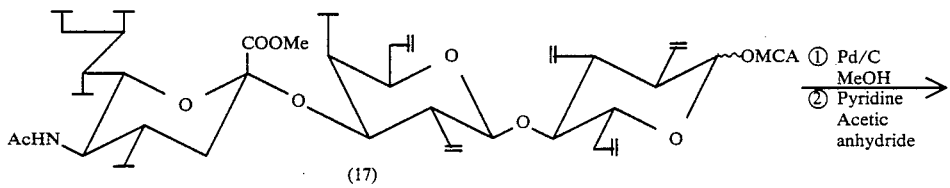
(17) →[① Pd/C MeOH ② Pyridine Acetic anhydride]
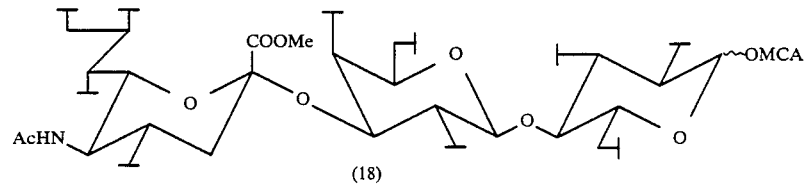
(18)
(18) →[AcONa Thiourea EtOH]
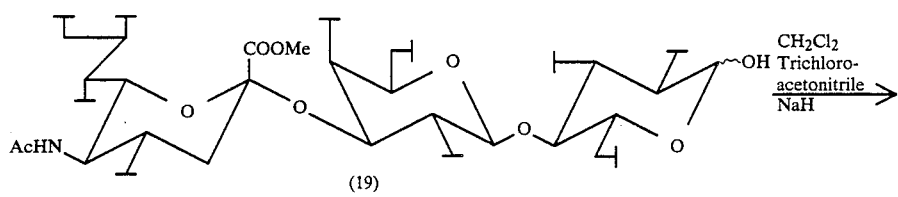
(19) →[CH₂Cl₂ Trichloro-acetonitrile NaH]

-continued
Scheme 4
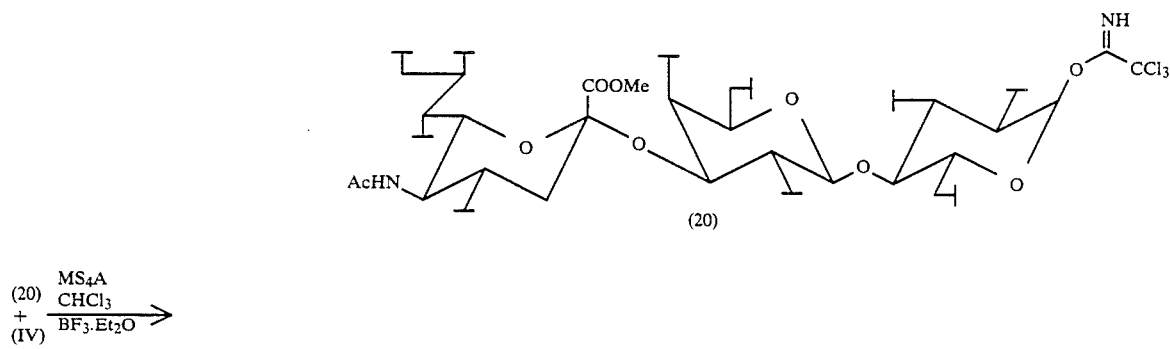
(20) + (IV) →[MS₄A, CHCl₃, BF₃·Et₂O]
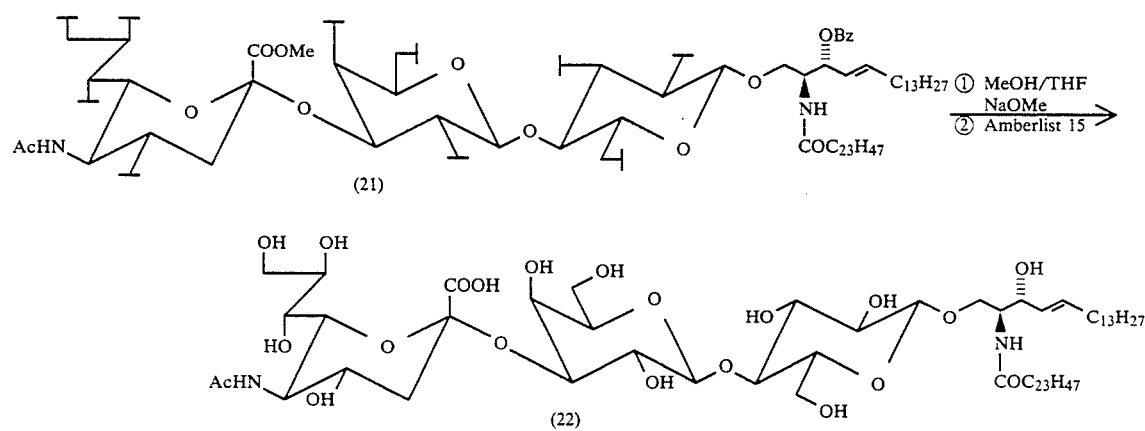
Scheme 5
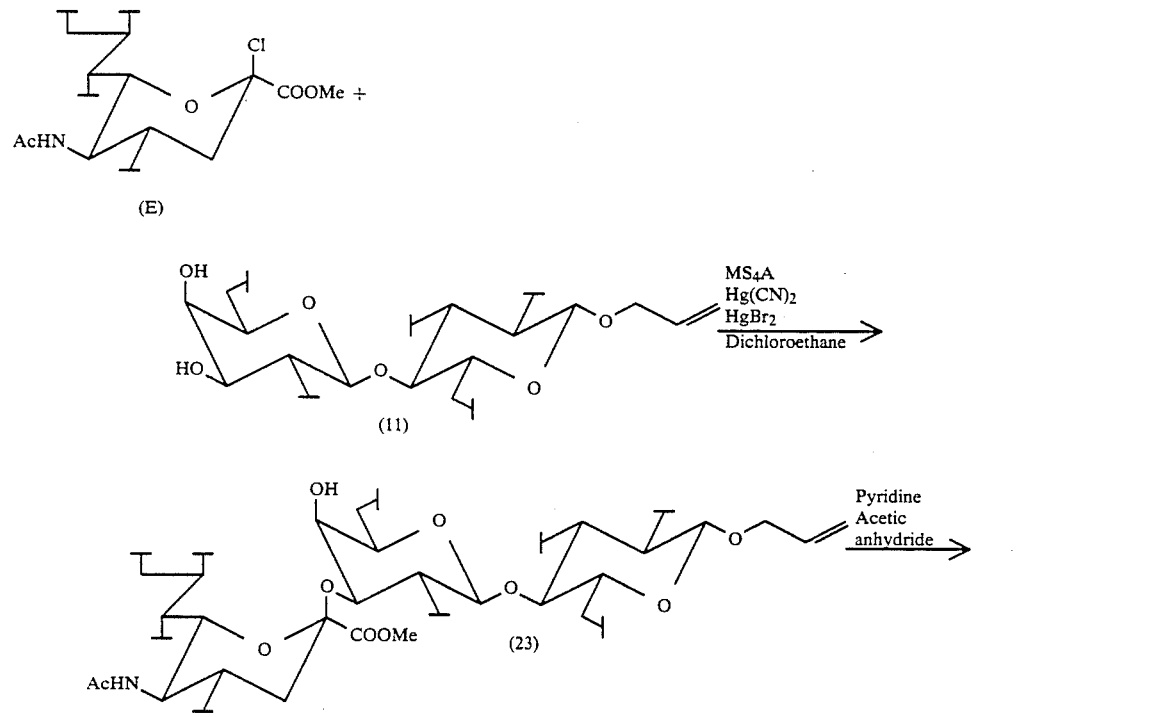

-continued
Scheme 5
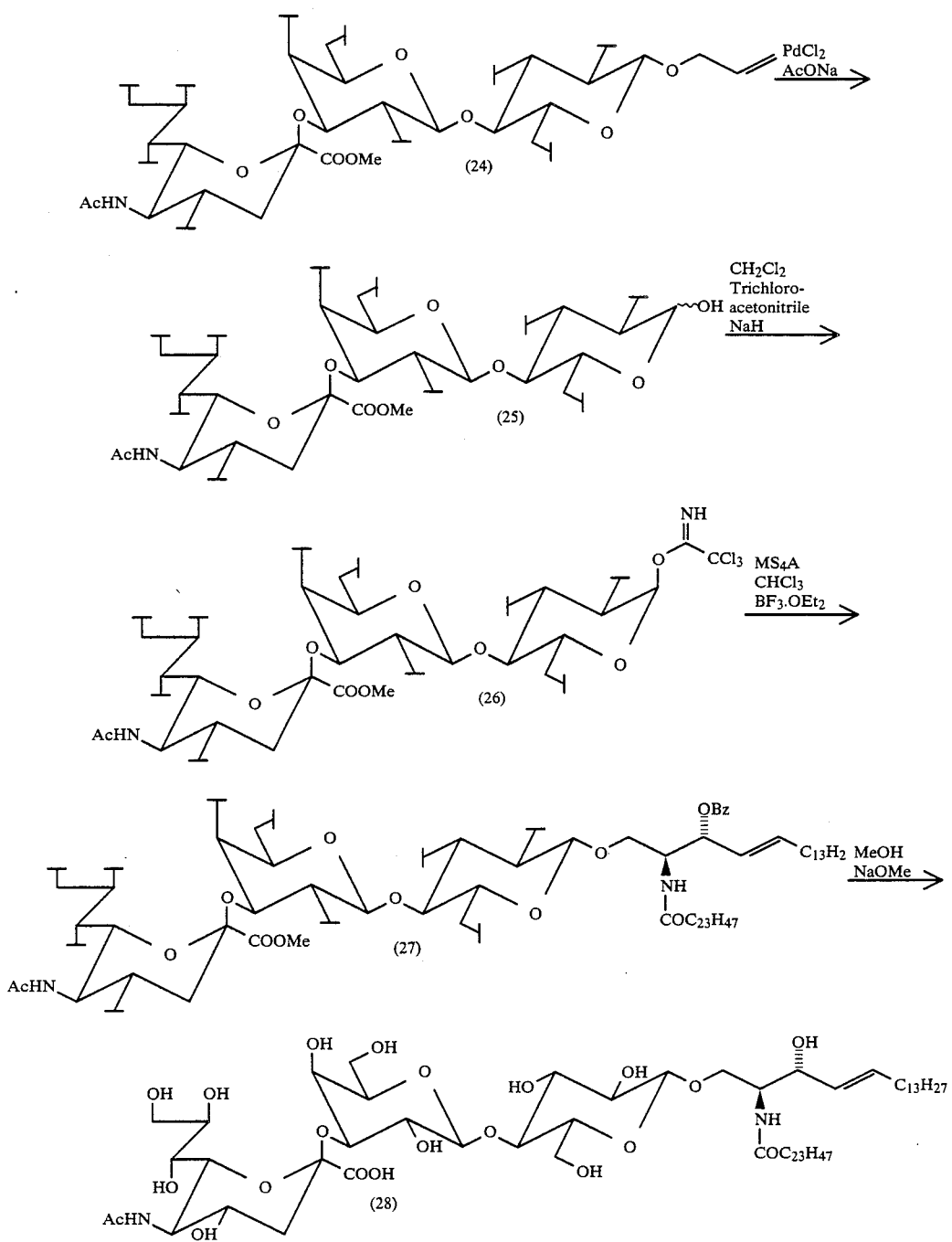

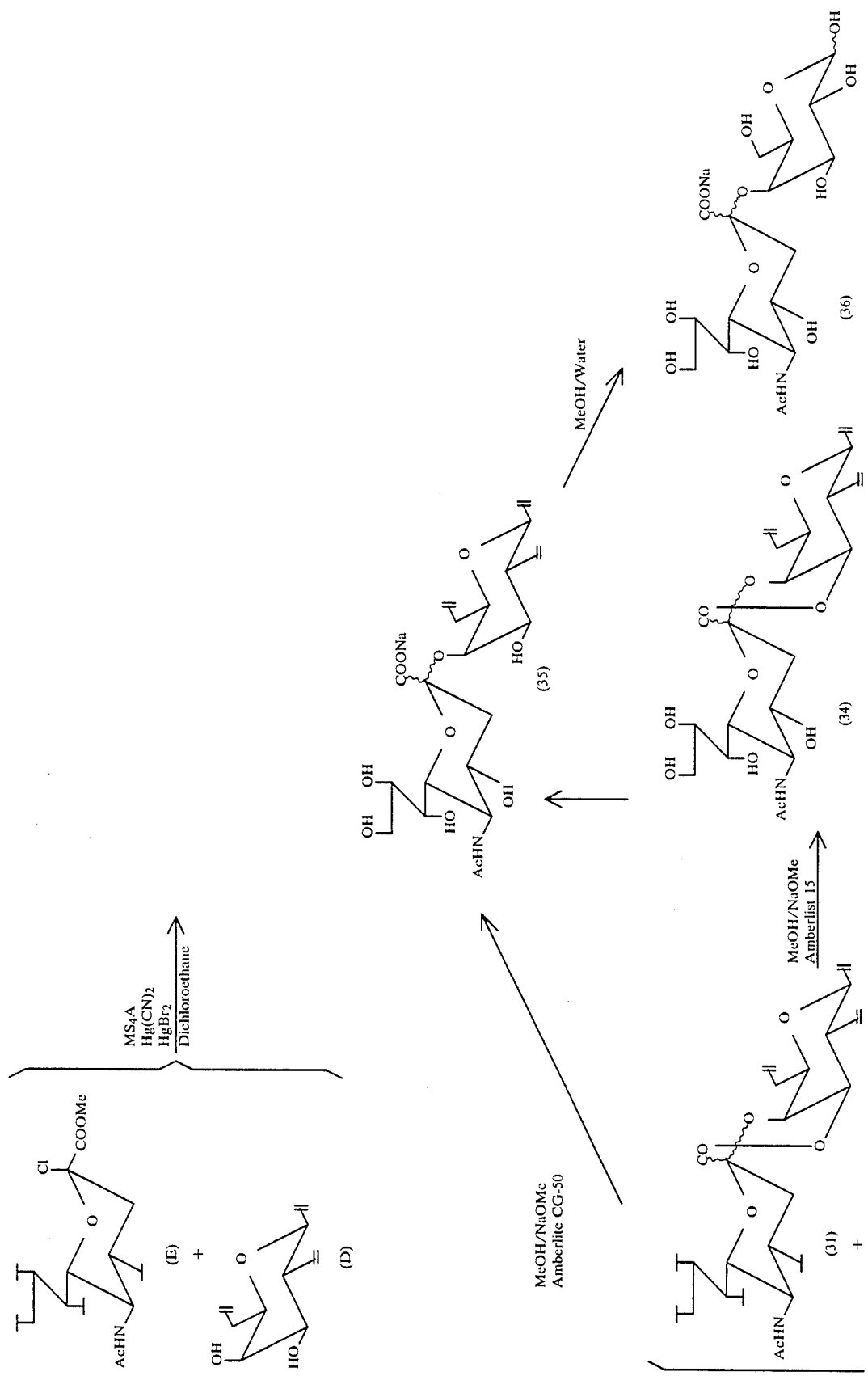

-continued
Scheme 6
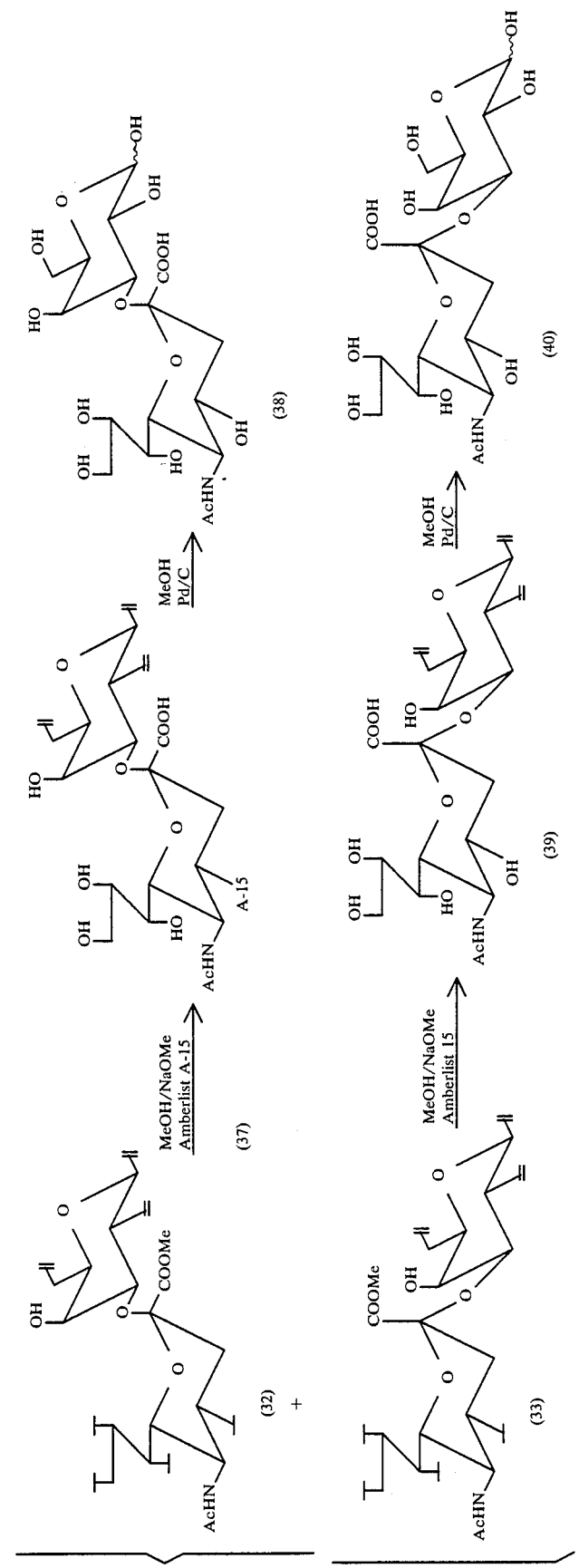

Scheme 7
(32) →[Pyridine Acetic anhydride]
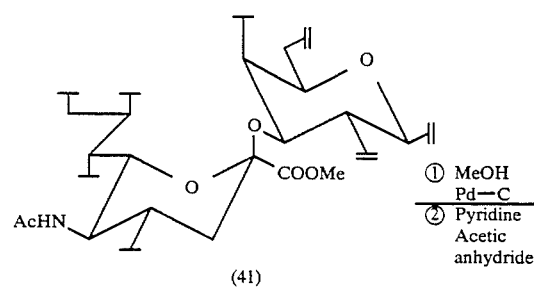
(41) →[① MeOH Pd—C ② Pyridine Acetic anhydride]
(42)
-continued Scheme 7
(33) →[Pyridine Acetic anhydride]
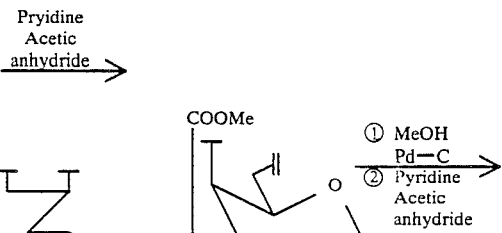
(43) →[① MeOH Pd—C ② Pyridine Acetic anhydride]
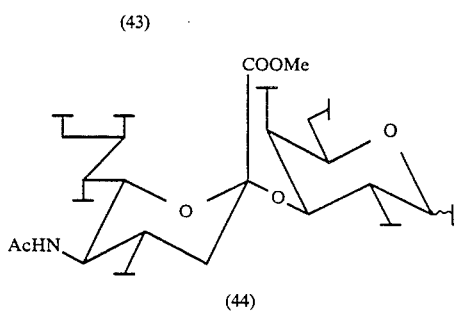
(44)
Scheme 8
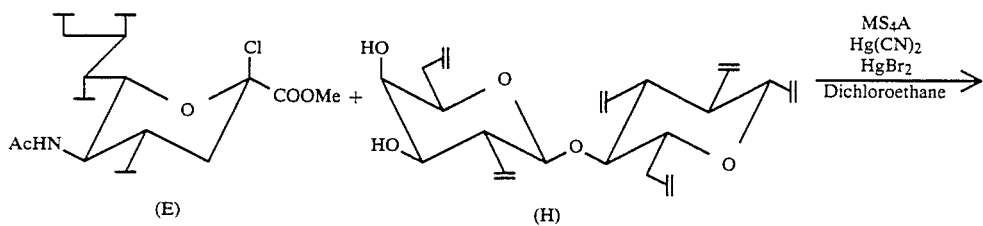
(E) + (H) →[MS₄A Hg(CN)₂ HgBr₂ Dichloroethane]
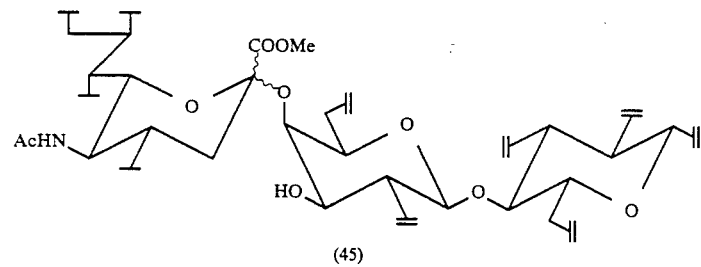
(45)
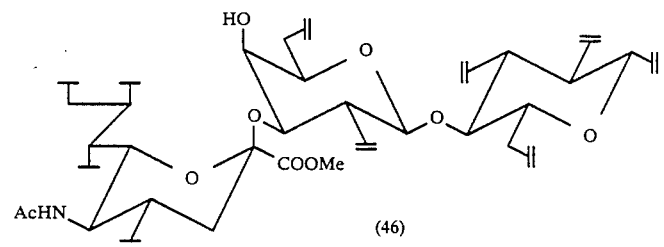
(46)

Scheme 8
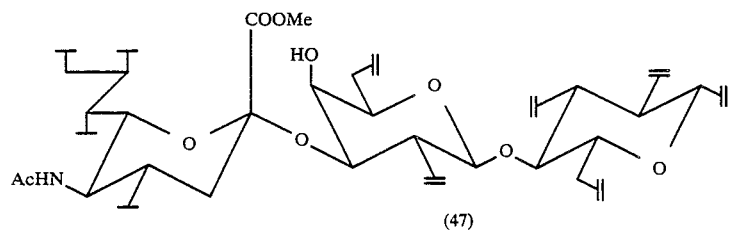
(47)
Scheme 9
(46) →[MeOH, NaOMe, Amberlist A-15]→ 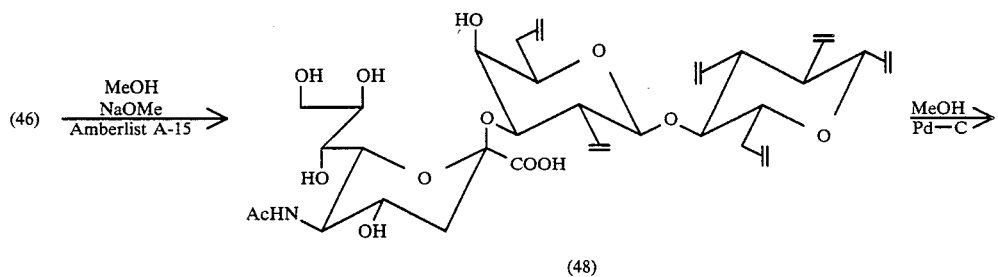 →[MeOH, Pd—C]→
(48)
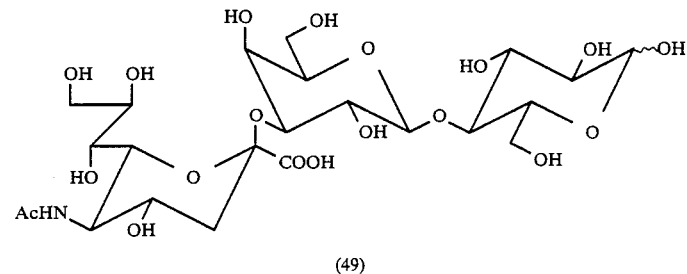
(49)
(47) →[MeOH, NaOMe, Amberlist A-15]→ 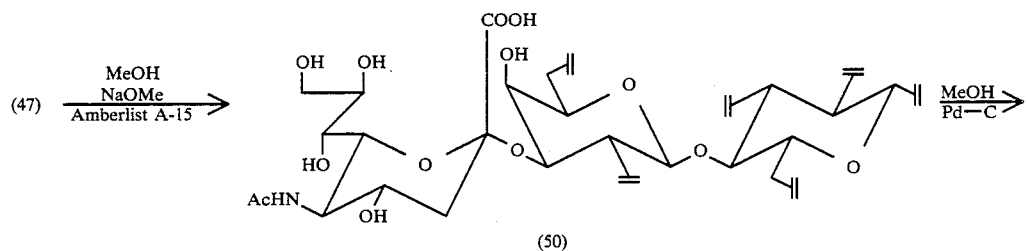 →[MeOH, Pd—C]→
(50)
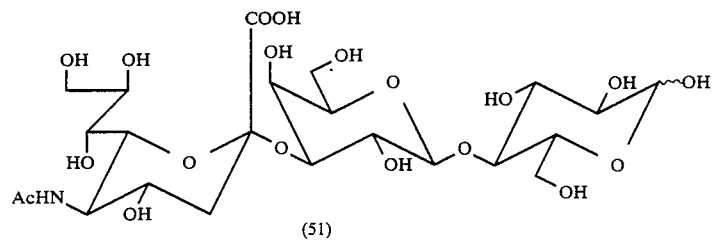
(51)

Scheme 10

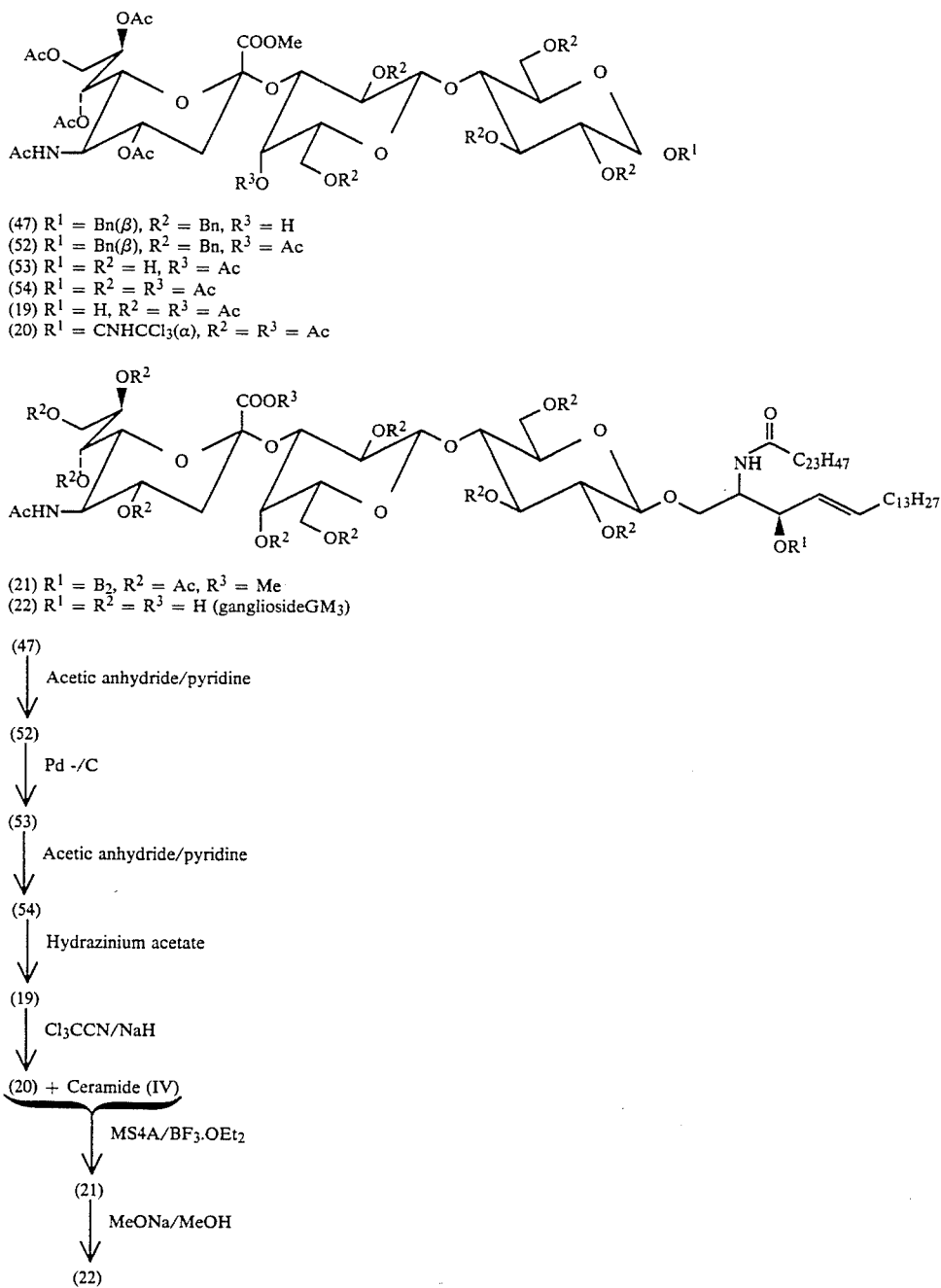

(47) $R^1 = Bn(\beta)$, $R^2 = Bn$, $R^3 = H$
(52) $R^1 = Bn(\beta)$, $R^2 = Bn$, $R^3 = Ac$
(53) $R^1 = R^2 = H$, $R^3 = Ac$
(54) $R^1 = R^2 = R^3 = Ac$
(19) $R^1 = H$, $R^2 = R^3 = Ac$
(20) $R^1 = CNHCCl_3(\alpha)$, $R^2 = R^3 = Ac$

(21) $R^1 = B_2$, $R^2 = Ac$, $R^3 = Me$
(22) $R^1 = R^2 = R^3 = H$ (gangliosideGM$_3$)

(47)
↓ Acetic anhydride/pyridine
(52)
↓ Pd -/C
(53)
↓ Acetic anhydride/pyridine
(54)
↓ Hydrazinium acetate
(19)
↓ Cl$_3$CCN/NaH
(20) + Ceramide (IV)
↓ MS4A/BF$_3$.OEt$_2$
(21)
↓ MeONa/MeOH
(22)

All the compounds thus obtained (4), (5), (6), (7), (8), (9), (10), (11), (12), (13), (14), (15), (16), (17), (18), (19), (20), (21), (22), (23), (24), (25), (26), (27), (28), (B), (C), (D), (G), (H), (31), (32), (33), (34), (35), (36), (37), (38), (39), (40), (41), (42), (43), (44), (45), (46), (47), (48), (49), (50), (51), (52), (53) and (54) are novel.

These new compounds of this invention may be employed as tumor markers, differentiation markers of cells having differentiation potency, or useful intermediates for the synthesis of various gangliosides.

This invention will now be explained in detail with reference to the following examples to which this invention is not limited.

An outline of Examples is as follows:

| Reference Example | | |
|---|---|---|
| 1 | (I) → (II) | Tritylation |
| 2 | (II) → (III) | Benzoylation |
| 3 | (III) → (IV) | Detritylation |
| 4 | (I) → (IV) | Benzoylation |
| Example | | |
| 1 | (1) → (2) | Allylation |
| 2 | (2) → (3) | Deacetylation |
| 3 | (3) → (4) + (5) | Isopropylidene deriv. |
| 4 | (4) + (5) → (6) + (7) | Benzylation |

| Reference Example | | |
|---|---|---|
| 5 | (6) → (8) | Deisopropylidene |
| 6 | (7) → (9) | Deisopropylidene |
| 7 | (4) → (10) | Acetylation |
| 8 | (10) → (11) | Deisopropylidene |
| 9 | (E) + (8) → (12) + (13) + (14) | Glycosidation |
| 10 | (13) → (15) | Acetylation |
| 11 | (15) → (16) | Deacetylation |
| 12 | (16) → (17) | Monochloro-acetylation |
| 13 | (17) → (18) | Debenzylation Acetylation |
| 14 | (18) → (19) | Demonochloro-acetylation |
| 15 | (19) → (20) | -C(NH)-CCl$_3$ deriv. |
| 16 | (IV) + (20) → (21) | Ceramide |
| 17 | (21) → (22) | Deacetylation and Debenzoylation |
| 18 | (E) + (11) → (23) | Glycosidation |
| 19 | (23) → (24) | Acetylation |
| 20 | (24) → (25) | Deallylation |
| 21 | (25) → (26) | -C(NH)-CCl$_3$ deriv. |
| 22 | (26) → (27) | Ceramide |
| 23 | (27) → (28) | Deactylation and Debenzoylation |
| 24 | (A) → (B) | Isopropylidene deriv. |
| 25 | (B) → (C) | Benzylation |
| 26 | (C) → (D) | Deisopropylidene |
| 27 | (F) → (G) | Benzylation |
| 28 | (G) → (H) | Deisopropylidene |
| 29 | (E) + (D) → (31) + (32) + (33) | Glycosidation |
| 30 | (31) → (34) | Deacetylation |
| 31 | (31) → (35) | Opening of lactone ring |
| 32 | (35) → (36) | Debenzylation |
| 33 | (32) → (37) | Deacetylation |
| 34 | (37) → (38) | Debenzylation |
| 35 | (33) → (39) | Deacetylation |
| 36 | (39) → (40) | Debenzylation |
| 37 | (32) → (41) | Acetylation |
| 38 | (41) → (42) | Debenzylation Acetylation |
| 39 | (33) → (43) | Acetylation |
| 40 | (43) → (44) | Debenzylation Acetylation |
| 41 | (E) + (H) → (45) + (46) + (47) | Glycosidation |
| 42 | (46) → (48) | Deacetylation |
| 43 | (48) → (49) | Debenzylation |
| 44 | (47) → (50) | Deacetylation |
| 45 | (50) → (51) | Debenzylation |
| 46 | (47) → (52) | Acetylation |
| 47 | (52) → (53) → (54) | Debenzylation Acetylation |
| 48 | (54) → (19) | Deacetylation |
| 49 | (19) → (20) | -C(NH)-CCl$_3$ deriv. |
| 50 | (20) → (21) | Ceramide |
| 51 | (21) → (22) | Deacetylation and Debenzoylation |

REFERENCE EXAMPLE 1

The compound (I) (325 mg, 0.5 mmol) was dissolved in dry pyridine (5 ml). Trityl chloride (TrCl) (278 mg, 1.0 mmol) was added. The mixture was stirred at room temperature for 24 hours and further at 55° C. for 4 hours. The solvent was evaporated in vacuo. The residue was dissolved in chloroform, washed with water, dried on MgSO$_4$ and concentrated in vacuo. The resulting residue was subjected to column chromatography (Wakogel C-300, 50g, hexane-ethylacetate=4:1) to give the compound (II) (297 mg, 66.6%).

(The Compound (II))

$(\alpha)^{22}_D$ −0.94° (C=0.96, CHCl$_3$)
Analysis: Calcd.: C,82.09; H,10.96; N,1.57. for (C$_{61}$H$_{97}$NO$_3$) Found: C,82.00 H,11.17 N,1.49.
Rf 0.34 (hexane-ethylacetate 4:1)

REFERENCE EXAMPLE 2

The compound (II) (224 mg, 0.25 mmol) was dissolved in pyridine (2 ml). Benzoyl chloride (70 mg, 0.5 mmol) and dimethylaminopyridine (30 mg) were added and the mixture was stirred at room temperature for 24 hours and at 55° C. for one hour, and concentrated in vacuo. The residue was dissolved in chloroform, washed with water, dried on MgSO4 and concentrated in vacuo. The resulting residue was subjected to column chromatography (Robar column Li Chroprep Si60 Groβe A, hexane-ethylacetate =4:1) to give the compound (III) (183 mg, 88.2%) and the compound (II) (38 mg)

(The Compound (III))

$(\alpha)^{19}_D$ 5.93° (CHCl$_3$, C=0.86)
Analysis: Calcd.: C,81.96; H,10.22; N,1.41. (for C$_{68}$H$_{101}$NO$_4$) Found: C,82.01; H,10.17; N,1.36.
Rf 0.34 (hexane: ethylacetate 4:1)

REFERENCE EXAMPLE 3

The compound (III) (163 mg, 0.164 mmol) was dissolved in CH$_2$Cl$_2$ (5 ml) and MeOH (2.5 ml). Paratoluenesulfonic acid monohydrate (16 mg) was added. The mixture was stirred at room temperature for 24 hours and concentrated in vacuo. The residue was subjected to column chromatography (Wakogel C-300, 10 g) and eluted with 3% methanol-containing chloroform to give the compound (IV) (104 mg, 84.3%).

(The Compound IV))

$(\alpha)^{23}_D$ +16.5° (CHCl$_3$, C=1.10)
Analysis: Calcd.: C,78.03; H,11.63; N,1.86. (for C$_{49}$H$_{87}$NO$_4$) Found: C,$_{77.85}$; H,11.54; N,1.84.

REFERENCE EXAMPLE 4

The compound (I) (975 mg, 1.5 mmol) was dissolved in pyridine (15 ml). TrCl (625 mg, 2.25 mmol) was added. The mixture was stirred at 55° C. for 4 hours and at room temperature for 24 hours. Benzoylchloride (315 mg, 2.25 mmol) and dimethylaminopyridine (183 mg, 1.5 mmol) were added and stirred at room temperature for 5 hours. The reaction mixture was concentrated in vacuo and the residue was dissolved in ethyl acetate. The solution was washed with water, dried on MgSO$_4$ and concentrated in vacuo. The residue was dissolved in CH$_2$Cl$_2$ (10 ml). Para-toluene sulfonic acid (100 mg) was added and stirred at room temperature for 24 hours. The reaction mixture was concentrated in vacuo. The residue was dissolved in ethyl acetate, washed with a saturated solution of sodium bicarbonate in diluted hydrochloric acid and then a saturated solution of sodium chloride in water, dried on MgSO4 and concentrated in vacuo. The residue was subjected to column chromatography (Wakogel C-300, 10 g) and eluted with 2% methanol-containing chloroform to give the compound (IV) (801.6 mg, 70.9%).

EXAMPLE 1 n-Bu$_3$Sn-O-CH$_2$CHCH$_2$ (80.7g, 0.23 mol) was dissolved in ethylene chloride (500 ml). Tin tetrachloride (31.0 ml) was added under ice-cooled condition. To this solution, there was added 250 ml of a solution of D-lactose octaacetate (1) (142g, 0.21 mol) in ethylene chloride. The reaction mixture was stirred at room temperature for 2.5 hours and then poured into a saturated KF solution. Insoluble products precipitated were filtered. The filtrate was washed with a saturated NaCl solution, dried on MgSO4 and concentrated in vacuo. The residue was subjected to column chromatography (silica gel 2 kg) and eluted with toluene-ethylacetate (1:1) to give the compound (2) (85.8 g, 57.8%).

(The Compound (2))

NMR 90MHz CHCl$_3$ δppm (TMS) 1.96, 2.04, 2.12, 2.06 (OCO$\underline{ch_3}$×7) 5.64~6.00 1Hm —CH$_2$—$\underline{CH}$=CH$_2$

EXAMPLE 2

The compound (2) (85.8 g, 0.127 mol) was dissolved in methanol (600 ml). N-NaOCH$_3$ solution (10 ml) was added and stirred at room temperature for 2 hours. Precipitated crystals were collected by filtration. The compound (3) (41.8 g, 86.2%) wa obtained.

(The Compound (3))

Analysis: Calcd.: C,47.12; H,6.85; (for C$_{15}$H$_{26}$O$_{11}$). Found: C,46.92; H,7.01.

EXAMPLE 3

The compound (3) (44.4 g, 0.116 mol) was suspended in acetone (550 ml) and DMF (550 ml). Para-toluene sulfonic acid (2.32 g) and 2,2-dimethoxypropane (25.4 g) were added and stirred at room temperature for 2 days. Triethylamine (10 ml) was added to the reaction mixture and then, concentrated in vacuo. Ethyl acetate was added to the residue to precipitate and collect a mixture of the compounds (4) and (5) (41.4 g, 91.1%). Rf 0.56 (CHCl3: MeOH 5 : 1)

(The Compound (4))

CMR D$_2$O (dioxane)
25.952, 27.740, —CH$_3$, 101.695
102.727 anomeric carbon
118.981 =CH$_2$ 134.096 —CH=

(The Compound (5))

CMR D$_2$O (dioxane)
18.421, 28.770, —CH$_3$, 101.695
103.321 anomeric carbon
119.090 =CH$_2$ 134.043 —CH=

EXAMPLE 4

The mixture of the compounds (4) and (5) (2.2 g, 5.2 mmol) was dissolved in DMF (50 ml). NaH (50% in oil) (1.87 g) was added and stirred at room temperature for 30 minutes. Under ice-cooled condition, there was added benzylbromide (6.67 g, 39.0 mmol) and stirred at room temperature for 24 hours. A small amount of methanol was added under ice-cooled condition. The reaction mixture was then stirred for 30 minutes and concentrated in vacuo. The residue was dissolved in ethyl acetate, washed with water, dried on MgSO$_4$ and concentrated in vacuo. The resulting residue was subjected to silica gel column chromatography (Wakogel C-300, 120 g) to give the compound (6) (2.47 g, 56.9%) and the compound (7) (1.66 g, 38.2%).

(The Compound (6))

Analysis: Calcd.: C,72.91; H,6.92 (for C$_{53}$H$_{60}$O$_{11}$). Found: C,72.79; H,6.87.

(The Compound (7))

Analysis: Calcd.: C,72.91; H,6.92; (for C$_{53}$H$_{60}$O$_{11}$). Found: C,72.95; H,6.93.

EXAMPLE 5

The compound (6) (2.47 g, 2.8 mmol) was dissolved in ml of 90% acetic acid solution in water and stirred at 60° C. for 3 hours. The reaction mixture was concentrated in vacuo. The residue was recrystallized from ether - hexane to give the compound (8) (1.24 g, 52.6%) as needle crystals.

(The Compound (8))

m.p. 112-3° C.
$(\alpha)^{20}_D$ +19.0° (CHCl$_3$, C=1.50)
Analysis: Calcd.: C,72.09; H,6.78 (for C$_{50}$H$_{56}$O$_{11}$). Found: C,72.10; H,6.80.

EXAMPLE 6

The compound (7) (1.66g, 1.9 mmol) was dissolved in 30 ml of 90% acetic acid solution in water and stirred at 60° C. for 3 hours. The reaction mixture was concentrated in vacuo. The residue was recrystallized from chloroform-hexane to give the compound (9) (1.01 g, 67.6%).

(The Compound (9))

m.p 159-160° C.
$(\alpha)^{20}_D$ +26.3° (CHCl$_3$, C=1.07)
Analysis:
Calcd.: C,72.09; H,6.78 (for C$_{50}$H$_{56}$O$_{11}$). Found: C,72.06; H,6.79.

EXAMPLE 7

The compound (4) (2.11 g, 5.0 mmol) was dissolved in acetic anhydride (15 ml) and pyridine (15 ml). The reaction mixture was stirred at room temperature for 24 hours and concentrated in vacuo. The residue was subjected to silicagel column chromatography (Wakogel C-300, 250g) and eluted with 3.5% MeOH-containing chloroform to give the compound (10) (2.31 g, 73.1%).

(The compound (10))

$(\alpha)$ $^{22}_D$ +6.70° (CHCl$_3$, C=1.15)
Analysis: (for C$_{28}$H$_{40}$O$_{16}$·½H$_2$O) Calcd.: C,52.41; H,6.44. Found.: C,52.31; H,6.24.

EXAMPLE 8

The compound (10) (15.5g, 23.9 mmol) was dissolved in 90% CF$_3$COOH solution and stirred at room temperature for 20 minutes. The reaction mixture was concentrated in vacuo. The residue was dissolved in ethyl acetate. The solution was washed with NaHCO$_3$ solution and then saturated NaCl solution, dried on MgSO$_4$ and concentrated in vacuo. The residue was subjected to silicagel column chromatography (Wakogel C-300, 300 g) and eluted with 4% MeOH-containing chloroform to give the compound (11) (11.0 g).

(The Compound (11))

$(\alpha)^{22}_D$ −8.380° CHCl$_3$, C=1.42

NMR CDCl$_3$ δppm (TMS) 2.04, 2.12, OCO$\underline{CH}_3$×5 5.64~6.00 1 Hm —$\underline{CH}$=CH$_2$ CMR 25 MHz CDCl$_3$ ppm 20.664, $\underline{CH}_3$CO—, 99.373, 100.933, anomeric carbon, 117.552,=$\underline{CH}_2$, 113.343, —$\underline{CH}$=CH$_2$ 169.603, 170.626, 170.821, 171.016, 171.211, —$\underline{C}$OCH$_3$

EXAMPLE 9

To activated molecular sieves 4A (2.2 g), there were added Hg(CN)$_2$ (504 mg), HgBr$_2$ (720 mg), the compound (8) (833 mg, 1.0 mmol) and ethylene chloride (3 ml) and the mixture was stirred for one hour under argon atmosphere. To this solution, there was added a solution of the compound (E) (506 mg, 1.0 mmol) prepared by the Kuhn method in dichloroethane (3 ml). The mixture was stirred at room temperature for 24 hours and then filtered. The insolubles were washed with ethyl acetate. The filtrate and the washings were combined, washed with water, dried on MgSO$_4$ and concentrated in vacuo. The residue was subjected to silicagel column chromatography (Wakogel C-300, 80 g) and eluted with toluene-ethylacetate (1:2) to give the compound (12) (99 mg, 7.6%), the compound (13) (91 mg, 7.0%) and the compound (14) (37 mg, 2.8%).

(The Compound (14))

NMR 400MHz CDCl$_3$ (TMS)ppm 1.750 lHtJ=12.94, (H-3 ax) 1.991, 2.063, 2.075, 2.101, s, OCO 2.409, 1H, dd, J=12.94, 4.63(H-3 eq), 3.685, 3H, s, O$\underline{CH}_3$, 7.183~7.447 25H (aromatic proton)

(The Compound (13))

NMR 400MHz CDCl$_3$(TMS)ppm 1.871, 1.882, 1.984, 2.014, 2.090, s, OCO 2.500, 1H dd J=12.94, 4.64(H-3 eq), 3.753, 3HS, O$\underline{CH}_3$, 7.207~7.413 25H (aromatic proton)

(The Compound (12))

NMR 400MHz CDCl$_3$ TMS ppm 1.720, 1.979, 1.988, 2.084, 2.122, s, OCOCH3, 2.528, 1H dd J=13.67, 4.39(H-3 eq), 3.663, 3H, s, OCH$_3$, 7.223~7.43,0 25H (aromatic proton)

EXAMPLE 10

The compound (13) (605 mg, 0.57 mmol) was dissolved in pyridine (10 ml) and acetic anhydride (10 ml). To this solution, there was added dimethylamino-pyridine (70 mg). The mixture was stirred at room temperature for 24 hours and then concentrated in vacuo. The residue was subjected to silicagel column chromatography (Wakogel C-300, 80 g) and eluted with toluene-ethylacetate (1:2) to give the compound (15) (452 mg, 72.6%).

(The Compound (15))

NMR 90MHz CDCl$_3$ δppm 1.76, 1.85, 1.96, 2.00, 2.01, 2.08 —OCO$\underline{CH}_3$, 3.83, s, O$\underline{CH}_3$, 7.06~7.40, aromatic proton

EXAMPLE 11

The compound (15) (410 mg, 0.34 mmol) was dissolved in 90% AcOH. To this solution, there were added AcONa (500 mg) and palladium chloride (540 mg). The mixture was stirred for 2 hours in an ultrasonic stirrer and then concentrated in vacuo. The residue was dissolved in ethylacetate. The solution was washed with water, dried on MgSO$_4$ and concentrated in vacuo. The residue was subjected to silicagel column chromatography (Wakogel C-300, 50g) and eluted with 10% MeOH-containing isopropyl ether to give the compound (16) (353 mg, 89%).

(The Compound (16))

Analysis: Calcd.: C, 63.53; H, 5.95; N, 1.07. (for C$_{69}$H$_{77}$NO$_{24}$) Found: C, 63,12 H, 5.99, N, 0.98.

EXAMPLE 12

The compound (16) (312 mg, 0.24 mmol) was dissolved in pyridine (7 ml). Dry monochloroacetic acid (312 mg) was added and stirred at room temperature for one hour, to which ethylacetate was added to dilute it. The solution was washed with saturated NaHCO$_3$ solution, diluted HCl and saturated NaCl solution, dried on MgSO$_4$ and concentrated in vacuo. The residue was subjected to silicagel column chromatography (Wakogel C-300, 40g) and eluted with 10% MeOH-containing isopropyl ether to give the compound (17) (257 mg, 77.6%).

(The Compound (17))

NMR CDCl$_3$ δppm TMS 1.80, 1.86, 1.97, 2.03, 2.04, 2.06, OCO$\underline{CH}_3$, 2.60, 1H m H-3 eq 3.84, O$\underline{CH}_3$ 7.10~7.40 (aromatic proton)

EXAMPLE 13

The compound (17) (91 mg, 0.065 mmol) was dissolved in methanol (3 ml). 10% Pd/C (50 mg) was added and catalytic reduction was carried out at room temperature for 24 hours. The reaction mixture was filtered to remove Pd/C and the filtrate was concentrated in vacuo. To the residue, there were added acetic anhydride (1.0 ml) pyridine (1.0 ml). The mixture was stirred at room temperature for 2.5 hours and concentrated in vacuo. The residue was subjected to silicagel column chromatography (Wakogel C-300, 10 g) and eluted with 4% MeOH-containing chloroform to give the compound (18) (61 mg, 81%).

(The Compound (18))

NMR (90MHz, CDCl$_3$ δppm) 1.88~2.04 OCOCH$_3$ x 11 3.86, s, 3H, —O$\underline{CH}_3$

EXAMPLE 14

The compound (18) (61 mg, 0.053 mmol) was dissolved in ethanol. To this solution, there were added thiourea (20 mg) and sodium acetate (4 mg). The mixture was heated and refluxed for 5 hours. The reaction mixture was concentrated in vacuo. The residue was dissolved in 4% MeOH-containing chloroform and subjected to silicagel column chromatography (Wakogel C-300, 10 g) to give the compound (19) (21 mg). The compound (18) (40 mg) was recovered.

(The Compound (19))

Rf 0.42 (5% MeOH-containing chloroform)
NMR 90MHz 1.88, 2.02, 2.10, 2.16, 2.24,
S OCO$\underline{CH}_3$, 3.85, s, O$\underline{CH}_3$

EXAMPLE 15

The compound (19) (20 mg, 0.0187 mmol) was dissolved in methylene chloride (0.5 ml) and trichloroacetonitrile (13.5 mg) was added. To this, there was added NaH (60% in oil) (1.0 mg) under ice-cooled condition and stirred for 2 hours. The mixture was concentrated in vacuo. The residue was subjected to silicagel column chromatography (Wakogel C-300, 5 g) and eluted with ethyl acetate to give the compound (20) (10.0 mg).

(The Compound (20))

Rf 0.33 (ethyl acetate)
NMR 90MHz (δ ppm) 8.60, NH, 6.50, d J=4.0 anomeric proton, 3.88, s, OC$\underline{H}_3$, 2.60, 1H, dd, J=4.0, J=13.0 (in CDCl$_3$)

EXAMPLE 16

To activated molecular sieves 4A (200g), there were added the compound (20) (10 mg, 0.009 mmol), the compound (IV) (12 mg, 0.018 mmol) and CHCl3 (0.2 ml). To this mixture, there was added BF$_3$.Et$_2$O (2.0 μl) with stirring. The mixture was stirred at room temperature for 24 hours. Insolubles were filtered and washed with CHCl3. The filtrate and the washings were combined and concentrated in vacuo. The residue was subjected to silicagel column chromatography (C-300, 10 g) and eluted with 4% MeOH-containing chloroform to give the compound (21) (4 mg).

(The Compound (21))

Rf 0.29 3% MeOH-containing chloroform
Analysis: Calcd.: C,61.91; H,8.16; N,1.56. (for C$_{93}$H$_{146}$N$_2$O$_{32}$) Found: C,62.41; H,8.01; N,1.48.

EXAMPLE 17

The compound (21) (4.0 mg) was dissolved in a mixed solvent of methanol and THF (1:1) (0.5 ml). N-NaOMe (0.1 ml) was added and stirred at room temperature for 2 hours. The mixture was concentrated. To the residue, there were added water (0.1 ml) and MeOH-THF (1:1) (0.5 ml) and stirred at room temperature for 2 hours. Amberlist A-15 (Tradename) was added to neutralize the mixture and then filtered. Amberlist A-15 was washed with methanol. The solution combined was concentrated in vacuo. The residue was washed with ether and dried to give the compound (22) (ganglioside GM3) (1.7 mg).

(The Compound (22))

Analysis: Calcd.: C,60.64; H, 9.32; N, 2.18. (for C$_{65}$H$_{119}$N$_2$O$_{21}$Na) Found: C, 60.21; H, 8.97; N, 2.10.

EXAMPLE 18

To activated molecular sieves 4A (20 g), there were added Hg(CN)$_2$ (5.04 g), HgBr$_2$ (7.20 g), the compound (11) (5.93g, 10 mmol) and dichloroethane (20 ml). The mixture was stirred for 30 minutes under argon atmosphere. The compound (E) (5.06 g, 10 mmol) prepared by the Kuhn method was dissolved in 10 ml of dichloroethane. Each of one fifth of this solution was added at 30 minute intervals. After the addition was completed, the mixture was stirred for 24 hours. The reaction mixture was filtered and insolubles were washed with ethyl acetate. The filtrate and the washings were combined, washed with water, dried on MgSO$_4$ and concentrated in vacuo. The residue was subjected to silicagel column chromatography (Wakogel C-300, 300 g) and eluted with 4% MeOHcontaining chloroform to give a fraction containing the compound (23). The fraction was further subjected to silicagel column chromatography (Wakogel C-300, 100 g) to give the compound (23) (634 mg, 6%).

(The Compound (23))

$(\alpha)^{24}_D$ −8.94° (CHCl$_3$, C=0.94)
NMR 400MHz (CDCl$_3$, δ ppm) 1.867, 1.982, 2.021, 2.027, 2.034, 2.056, 2.070, 2.077. 2.136, 2.140, OCOCH$_3$, 2.637, 1H, dd J=4,89, 13.43 Hz H-3eq, 3.832, 3H, s —OC$\underline{H}_3$, 5.777~5.862 1H, m, —OCH$_2$ —C$\underline{H}$=CH$_2$

EXAMPLE 19

To the compound (23) (266 mg, 0.25 mmol), there were added acetic anhydride (1.0 ml) and pyridine (1.0 ml). The mixture was stirred at room temperature for 24 hours and concentrated in vacuo. The residue was subjected to column chromatography (Robar column, size β) and eluted with 4% MeOHcontaining chloroform to give the compound (24) (257 mg, 92.7%).

(The Compound (24))

$(\alpha)^{22}_D$ −6.94° (CHCl$_3$, C=0.72)
NMR 400MHz (CDCl$_3$δ ppm) 1.795, 1H t,J=12.21 Hz 3Hax, 2.429, 1H, dd, J=4.63, 13.42 Hz, 3H, eq, 3.84, 3H, s, OC$\underline{H}_3$, 5.790~5.872, m, 1H, —CH$_2$ —C$\underline{H}$=CH$_2$

EXAMPLE 20

The compound (24) (216 mg, 0.195 mmol) was dissolved in 90% AcOH (3.0 ml). To this solution, there were added palladium chloride (41 mg) and sodium acetate (38 mg). The mixture was stirred for 5 hours in an ultrasonic stirrer, filtered and concentrated in vacuo. The residue was dissolved in ethyl acetate. The solution was washed with saturated NaHCO3 solution and NaCl solution, dried on MgSO4 and concentrated in vacuo. The residue was subjected to silicagel column chromatography (Wakogel C-300, 10 g) and eluted with 4% MeOH-containing chloroform to give the compound (25) (117 mg, 56%).

(The Compound (25))

NMR 90MHz (CDCl$_3$, δ ppm) 1.92~2.32, OCOCH$_3$×11, 3.86 —OC$\underline{H}_3$

EXAMPLE 21

Trichloroacetonitrile (68 mg) and NaH (60% in oil) (5 mg) were added under ice-cooled condition with stirring to a solution of the compound (25) (125 mg, 0.117 mmol) in dichloromethane (1.0 ml). The mixture was stirred for 2 hours, filtered through Celite (Tradename) and concentrated. The residue was subjected to silicagel column chromatography (Wakogel C-300, 5 g) and eluted with ethyl acetate to give the compound (26) (99 mg, 69.7%).

(The Compound (26))

NMR 90MHz (CDCl$_3$, δ ppm) 3.88, s, —OC$\underline{H}_3$, 6.46, 1H, d, anomeric proton, 8.68, s, =NH

EXAMPLE 22

To activated molecular sieves 4A (0.5 g), there were added the compound (26) (43 mg, 0.035 mmol), the compound (IV) (27 mg, 0.035 mmol) and CHCl3 (0.5 ml). BF$_3$ . OEt$_2$ (5 μ 1) was added to the mixture with stirring under ice-cooled condition. The mixture was stirred at room temperature for 24 hours. After the filtration, insolubles were washed with chloroform. The filtrate and the washings were combined and concentrated in vacuo. The residue was subjected to silicagel column chromatography (Wakogel C-300, 12 g) and eluted with 3% MeOHcontaining chloroform to give the compound (27)(23 mg).

(The Compound (27))

$(\alpha)^{25}_D$ +4.15° (C=0.65, CHCl$_3$) NMR 400MHz (CDCl$_3$, δ ppm) 0.87—CH$_2$CH$_3$, 1.25—(CH$_2$)$_n$—, 1.90, 1.98, 2.02, 2.29, OCOCH$_3$, 3.82, —OCH$_3$, 7.30~8.00 (aromatic proton)

EXAMPLE 23

The compound (27) (27 mg, 0.015 mmol) was dissolved in methanol (0.5 ml). N-NaOMe (0.036 ml) was added to this solution and stirred at room temperature for 4 hours. THF (0.5 ml) was added to dissolve the crystals precipitated. The mixture was stirred for additional two hours and concentrated in vacuo. To the residue, there were added 80% MeOH solution (3.0 ml) in water and THF (3.0 ml). The mixture was stirred at room temperature for 5 hours and concentrated in vacuo. Water was added to the residue. Insolubles were collected to give the compound (28) (12.7 mg, 65.8%).

(The Compound (28))

$(\alpha)^{25}_D$ −7.65° (CHCl$_3$ —MeOH 1:1 C=0.55) NMR 400MHz (d.6 DMSO . D$_2$O 98/2) δ ppm, 0.85, —CH$_2$CH$_3$, 1.23 —(CH$_2$)$_n$, 1.85 NHCOCH$_3$ 4.17 anomeric proton

EXAMPLE 24

Benzyl galactoside (the compound A) (8.1 g, 30 mmol) was suspended in acetone (150 ml). To this suspension, there were added paratoluenesulfonic acid (600 mg) and 2,2-dimethoxypropane (4.32 g). The mixture was stirred at room temperature for 2 hours. After triethylamine (2 ml) was added, the reaction mixture was concentrated in vacuo. The residue was subjected to silicagel column chromatography (SiO$_2$ C-300, 300 g) and eluted with toluene-ethyl acetate (1:2) to give the compound B (6.2 g, 66.7%).

(The Compound B)

Rf=0.58 (EtOAc)
$(\alpha)^{24}_D$ −2.38° (CHCl$_3$, C=1.08)
Analysis: Calcd.: C, 61.92; H, 7.15 (for C$_{16}$H$_{22}$O$_6$). Found: C, 61.63; H, 7.13.

EXAMPLE 25

50% NaH (46 mg) was washed with hexane and added to a solution of the compound B (100 mg, 0.32 mmol) in DMF (3 ml). The solution was stirred at room temperature for 30 minutes and then ice-cooled, to which benzylbromide (165 mg) was added. The mixture was stirred at room temperature for one hour and MeOH (1 ml) was added. Ethyl acetate and saturated NaCl solution were added and shaked. The ethyl acetate layer was dried on MgSO$_4$ and concentrated in vacuo. The residue was subjected to silicagel column chromatography (SiO$_2$ C-300, 10 g) and eluted with toluene-ethyl acetate (10:1) to give the compound C (111 mg, 70.2%).

(The Compound C)

Rf 0.55 (toluene-ethyle acetate=1:1)
$(\alpha)^{25}_D$ +7.25° (CHCl$_3$, C=1.02)
Analysis: Calcd.: C, 73.45; H, 6.99 (for C$_{30}$H$_{34}$O$_6$). Found: C, 73.38; H, 6.98.

EXAMPLE 26

The compound C (12.3 g, 25 mmol) was dissolved in 80% AcOH (50 ml) and stirred at 60° C. for 3 hours. The reaction mixture was concentrated in vacuo. The residue was washed with ether to give the compound D as needle crystals (5.2 g, 46%).

(The Compound D)

m.p. 107–108° C.
Rf 0.17 (toluene-ethyle acetate 10:1)
$(\alpha)^{26}_D$ −15.1° (CHCl$_3$ C=1.00)
Analysis: Calcd.: C, 71.98; H, 6.71 (for C$_{27}$H$_{30}$O$_6$). Found: C, 72.41; H, 6.75.

EXAMPLE 27

50% NaH (1.07 g) was washed with hexane and suspended in DMF (10 ml), to which the isopropylidene derivative F (1.41 g, 3.00 mmol) dissolved in DMF (20 ml) was added and stirred at 0° C. for 30 minutes, to which benzylbromide (2.7 ml) was added. The mixture was stirred at room temperature overnight and then cooled to 0° C. Methanol was added thereto. DMF was distilled off. The residue was dissolved in ethyl acetate. The solution was washed with water, dried on MgSO4, concentrated in vacuo, subjected to silicagel column chromatography (SiO$_2$ C-300, 70 g) and eluted with tolueneethylacetate (9:1) to give the compound G (1.725 g, 62.1%).

(The Compound G)

Rf 0.64 (toluene-ethyl acetate=4:1)
$(\alpha)^{22}_D$ +9.4° (CHCl$_3$, C=1.49)

EXAMPLE 28

The compound G (5.11 g, 5.53 mmol) was dissolved in AcOH (50 ml), to which water (10 ml) was added. The mixture was stirred at 60° C. for 2 hours and concentrated in vacuo. The resulting solid was suspended in and washed with hexane to obtain the compound H (4.82 g, 98.5%).

(The Compound H)

m.p. 86~88° C.
$(\alpha)^{22}_D$ +19.5° (CHCl$_3$, C=1.20)
Rf 0.35 (toluene-ethyl acetate=4:1)
Analysis: Calcd.: C, 73.45; H, 6.62 (for C$_{54}$H$_{58}$O$_{11}$). Found: C, 73.52; H, 6.50.

EXAMPLE 29

To activated molecular sieves 4A (15 g), there were added Hg(CN)$_2$ (3.03 g), HgBr$_2$ (1.44 g), the compound D (1.80 g, 4 mmol) and dichloroethane (6 ml). The mixture was stirred for one hour under argon atmosphere. To this solution, there was added one half of a solution of the compound E prepared from N-acetyl neuraminic acid acetate methyl ester (2.13 g, 4 mmol) in dichloroethane (6 ml), after one hour, the other half thereof and the mixture was stirred at room temperature overnight. The reaction mixture was filtered. Insolubles were washed with ethyl acetate. The filtrate and the washings were combined, washed with saturated NaCl solution three times, dried on MgSO$_4$ and concentrated in vacuo. The residue was subjected to silicagel column chromatography (SiO$_2$ C-300, 80 g) and eluted with toluene-ethyl acetate (1:2) to give the compound (31) (82 mg) and a mixture of the compounds (32) and (33) (15% from N-acetyl neuraminic acid acetate methyl ester). The mixture was subjected to Robar column (β-size) and eluted with 10% MeOH-containing toluene to separate the compound (33) (-anomer, 190 mg) and the compound (32) (β-anomer, 300 mg).

(The Compound (31))

m.p. 147~152° C.

$(\alpha)^{23}_D$ +11.3° (C=1.80, CHCl$_3$)

Analysis: Calcd.: C, 61.32; H, 6.04; N, 1.55. (for C$_{46}$H$_{53}$NO$_{17}$·½H$_2$O) Found: C, 61.30; H, 5.99; N, 1.53.

(The Compound (32) β-anomer)

$(\alpha)^{29}_D$ −25.4° (C=1.40, CHCl$_3$)

Analysis: Calcd.: C, 61.09; H, 6.21; N, 1.52. (for C$_{47}$H$_{57}$NO$_{18}$) Found: C, 60.90; H, 6.27; N, 1.48.

Rf 0.24 (toluene-methanol 10:1)

(The Compound (33) α-anomer)

$(\alpha)^{29}_D$ −21.7° (C=1.15, CHCl$_3$)

Analysis: Calcd. C, 61.09; H, 6.21; N, 1.52. Found C, 60.92; H, 6.25; N, 1.54.

Rf 0.20 (toluene-methanol 10:1)

EXAMPLE 30

The compound (31) (60 mg) was dissolved in MeOH (2.0 ml). N-NaOCH$_3$ (0.3 ml) was added. The mixture was stirred at room temperature for 24 hours, then neutralized by Amberlist A-15 (Tradename) and filtered. The filtrate was concentrated in vacuo to give the compound (34) as crystalline powder (33 mg, 67.8%).

(The Compound (34))

Analysis: Calcd.: C, 61.53; H, 6.39; N, 1,89. (for C$_{38}$H$_{45}$NO$_{13}$ · H$_2$O) Found: C, 61.52; H, 6.29; N, 1.82.

Rf 0.88 (BuOH:EtOH:H$_2$O=4:2:2)

EXAMPLE 31

The compound (31) (200 mg) was dissolved in MeOH (12 ml), to which N-NaOMe (1.1 ml) was added. The mixture was stirred at room temperature for 24 hours, neutralized by Amberlite CG-50 (Tradename) and then filtered through Celite (Tradename). The residue was subjected to column chromatography (silanized silica-gel, 10 g) and eluted with MeOH - H$_2$O (1:2) to give the compound (35) (109 mg, 63.6%).

(The Compound (35))

Rf 0.69 (BuOH:EtOH:H$_2$O=4:2:2) NMR 400MHz D$_2$O δ ppm, (acetone) 1.656, 1H t (H-3 ax), 2.664, 1Hd (H-3 eq) 2.019 3H S NHCOCH$_3$, 6.979~7.314 15H (aromatic proton)

EXAMPLE 32

The compound (35) (108 mg) was dissolved in MeOH - H2O (9:1) (5 ml). Catalytic reduction was carried out at room temperature for 24 hours and then at 60° C. for 5 hours. The reaction mixture was concentrated in vacuo. The residue was subjected to Robar column (PR-8, size A) and eluted with MeOH —H$_2$O (80:1) to give the compound (36) (23.1 mg, 33.1%).

(The Compound (36))

Rf 0.34 (BuOH:EtOH:H$_2$O=4:2:2)

NMR 400MHz D$_2$O δ ppm, (acetone) 2.054, NHCOCH$_3$, 1.618~1.704, 1Hm H-3 ex 2.494~2.607, 1H m H-3 eq

EXAMPLE 33

The compound (32) (106 mg, 0.11 mmol) was dissolved in MeOH (3 ml), to which N-NaOMe (0.3 ml) was added. The mixture was stirred at room temperature for 24 hours, neutralized by Amberlist A-15 (tradename), and then concentrated in vacuo. The residue was subjected to Robar column (RP-18, size β) and eluted with MeOH —H$_2$O (3:1) to give the compound (37) (60 mg, 70.5%).

(The Compound (37))

Rf 0.34 (BuOH:EtOH: H$_2$O=4:2:2)

Analysis: (for C$_{38}$H$_{47}$NO$_4$) Calcd.: C, 61.53; H, 6.39; N, 1.89. Found: C, 61.20; H, 6.31; N, 1.52.

EXAMPLE 34

The compound (37) (63 mg) was dissolved in MeOH (2.0 ml), to which 10% Pd-C (63 mg) was added. Catalytic reduction was carried out for 24 hours. The reaction mixture was filtered to remove Pd-C and concentrated in vacuo to give almost quantitatively the compound (38).

(The Compound (38))

Rf 0.26 (BuOH:EtOH:H$_2$O=4:2:2)

$(\alpha)^{19}_D$ +11.0° (C=0.30, water)

EXAMPLE 35

The compound (33) (260 mg, 0.28 mmol) was dissolved in MeOH (5 ml), to which N-NaOMe (1.12 ml) was added. The mixture was stirred at room temperature for 24 hours, neutralized by Amberlist A-15 (tradename), filtered and concentrated in vacuo. The residue was subjected to Robar column (RP-18, size β) and eluted with MeOH - H$_2$O (3:1) to give the compound (39) (120 mg, 57.5%).

(The Compound (39))

Rf 0.64 (BuOH:EtOH:H$_2$O=4:2:2)

$(\alpha)^{25}_D$ −25.9° (C=1.62, CH$_3$OH)

Analysis: Calcd.: C, 61.53; H, 6.39; N, 1.89. (for C$_{38}$H$_{47}$NO$_4$) Found: C, 61.15; H, 6.05; N, 1.94.

EXAMPLE 36

The compound (39) (108 mg, 0.146 mmol) was dissolved in MeOH (5 ml), to which 10% Pd-C (200 mg) was added. Catalytic reduction was carried out for 24 hours. The mixture was filtered to remove Pd-C and concentrated in vacuo to give the compound (40) (68 mg, about 100%).

(The Compound (40))

Rf 0.37 (BuOh:EtOH: H$_2$O=4:2:2)

$(\alpha)^{19}_D$ (BuOH: EtOH: H$_2$O)

EXAMPLE 37

The compound (32) (577 mg, 0.625 mmol) was dissolved in acetic anhydride (10 ml) and pyridine (10 ml). The mixture was stirred at room temperature for 24 hours. The reaction mixture was concentrated in vacuo. The residue was subjected to silicagel column chromatography (SiO$_2$ C-300, 80 g) and eluted with toluene-ethyl acetate (1:2) to give the compound (41) (477 mg, 79.1%).

(The Compound (41))

Rf 0.56 (15% MeOH-containing isopropylether)

$(\alpha)^{23}_D$ −23.9° (CHCl$_3$, C=1.03)

Analysis: Calcd.: C, 60.92; H, 6.16; N, 1.45. (for C$_{49}$H$_{59}$NO$_{19}$) Found: C, 60.69; H, 6.18; N, 1.41.

EXAMPLE 38

The compound (41) (379 mg, 0.39 mmol) was dissolved in MeOH (15 ml), to which 10% Pd-C (200 mg) was added. Catalytic reduction was carried out at room temperature for 24 hours. After filtration, the mixture was concentrated in vacuo. The residue was dissolved in a mixed solvent of acetic anhydride (5 ml) and pyridine (5 ml) and stirred at room temperature for 3 hours. The reaction mixture was concentrated in vacuo. The residue was dissolved in ethyl acetate, washed with water, dried on MgSO$_4$ and concentrated in vacuo. The residue was subjected to silicagel column chromatography (C-300, 20 g) and eluted with 15% MeOH-containing isopropylether to give the compound (42) (181 mg, 61.7%).

(The Compound (42))

Rf 0.20 (3% MeOH-containing chloroform)

NMR 400Hz CDCl$_3$ δ ppm, (TMS), 1.799, 1H t J=11.96, H-3 ex 2.585 1H dd J=13.19, 4.64, H-3 eq, 3.748 3H S OCH$_3$

EXAMPLE 39

The compound (33) (195 mg, 0.211 mmol) was dissolved in acetic anhydride (10 ml) and pyridine (10 ml). The mixture was stirred at room temperature for 24 hours and concentrated in vacuo. The residue was subjected to silicagel column and Robar column (β-size) and eluted with toluene-ethylacetate (1:2) to give the compound (43) (148 mg, 72.6%).

(The Compound (43))

$(\alpha)^{23}_D$ −30.7° (CHCl$_3$, C=1.25)

Analysis: Calcd.: C, 60.92; H, 6.16; N, 1.45. (for C$_{49}$H$_{59}$NO$_{19}$) Found: C, 61.65; H, 6.28; N, 1.33.

EXAMPLE 40

The compound (43) (99 mg, 0.10 mmol) was dissolved in MeOH (5 ml), to which 10% Pd-C (100 mg) was added. Catalytic reduction was carried out at room temperature for 24 hours. The reaction mixture was filtered to remove Pd-C and concentrated in vacuo. The residue was dissolved in acetic anhydride (1 ml) and pyridine (1 ml), stirred at room temperature for 24 hours and concentrated in vacuo. The residue was subjected to Robar column (size A) and eluted with ethyl acetate - toluene (2:1) to give quantitatively the compound (44) (77 mg).

(The Compound (44))

Rf 0.25 (3% MeOH-containing chloroform)

NMR 400MHz CDCl$_3$ δ ppm, (TMS), 1.711, 1H t J=12.45, H-3 ax 1.856~2.229, 27H, OCOC$\underline{H}_3$, 2.583~2.642 m, 1H, H-3ax, 3.863, s, OC$\underline{H}_3$

EXAMPLE 41

The compound H (3.85 g, 4.4 mmol), Hg(CN)$_2$ (1.36 g) and HgBr$_2$ (648 mg) were added to molecular sieves 4A (7.2 g), to which dichloroethane (5 ml) was added under argon atmosphere and stirred at room temperature for one hour. To this solution, there were added one half of a solution of N-acetyl-D-acetyl neuraminyl chloride (the compound E) (916 mg, 1.8 mmol) in dichloroethane (5 ml) and after one hour, the remaining half of the solution. The reaction mixture was stirred at room temperature for 2 days and filtered. Insolubles were washed with ethyl acetate. The filtrate and the washings were combined, washed with water, dried on MgSO4 and concentrated in vacuo. The residue was subjected to silicagel column chromatography (C-300, 180 g) and eluted with toluene - ethyl acetate (1:2) to give the compound (45) (93 mg, 3.8%) and a mixture of the compounds (46) and (47) (425 mg, 17.4%). The mixture (425 mg) was subjected to Robar column (size β) and eluted with 10% MeOH-containing toluene to give the compound (46) (β-anomer, 255 mg) and the compound (47) α-anomer, 100 mg).

(The Compound (45))

(Rf 0.49, 15% MeOH-containing isopropylether)

Analysis: Calcd.: C, 65.52; H, 6.32; N, 1.03. (for C$_{74}$H$_{85}$NO$_{23}$) Found: C, 65.27; H, 6.07; N, 1.00.

(The Compound (46))

$(\alpha)^{23}_D$ +3.10° (C=1.065, CHCl$_3$)

Rf 0.31, 10% MeOH-containing toluene)

Analysis: Calcd.: C, 65.52; H, 6.32; N, 1.03. (for C$_{74}$H$_{85}$NO$_{23}$) Found: C, 65.64; H, 6.33; N, 1.05.

(The Compound (47))

$(\alpha)^{23}_D$ +5.84° (C=0.925, CHCl$_3$)

(Rf 0.26, 10% MeOH-containing toluene)

Analysis: Calcd. C, 65.52; H, 6.32; N, 103. (for C$_{74}$H$_{85}$NO$_{23}$) Found C, 65.40; H, 6.25; N, 1.10.

EXAMPLE 42

The compound (46) (136 mg, 0.1 mmol) was dissolved in MeOH (5 ml), to which N-NaOMe (0.8 ml) was added. The mixture was stirred at room temperature for 24 hours, neutralized by Amberlist A-15 (tradename), filtered to remove the resin and concentrated in vacuo. 0.1 N-NaOH solution (1.0 ml) was added to the residue. The mixture was stirred at room temperature for 24 hours, neutralized by Amberlist A-15 (tradename), filtered and concentrated in vacuo to give the compound (48) (96 mg, 80.6%).

(The Compound (48))

Rf 0.70 BuOH:EtOH:H$_2$O (4:2:2)

$(\alpha)^{19}_D$ +6.62° (C=0.71, MeOH)

EXAMPLE 43

The compound (48) (84 mg, 0.071 mmol) was dissolved in MeOH (5 ml), to which 10% Pd-C (100 mg) was added. Catalytic reduction was carried out at room temperature for 2 days. The mixture was filtered to remove Pd-C and concentrated to give the compound (49) (42 mg, 93.7%).

(The Compound (48))

Rf 0.19 BuOH:EtOH:H$_2$O (4:2:2)

$(\alpha)^{19}_D$ +11.6° (C=1.08, H$_2$O)

EXAMPLE 44

The compound (47) (136 mg, 0.1 mmol) was dissolved in MeOH (5 ml), to which N-NaOMe (0.6 ml) was added. The mixture was stirred at room temperature for 24 hours, neutralized by Amberlist A-15 (tradename), filtered and concentrated in vacuo. The residue was mixed with 0.1 N-NaOH solution (1.0 ml) and MeOH (2.0 ml) and stirred at room temperature for 7 hours. The reaction mixture was neutralized by Amberlist A-15 (tradename) and concentrated in vacuo to give the compound (50) (97 mg, 81.4%).

(The Compound (50))

Rf 0.65 BuOH:EtOH:H2O (4:2:2) $(\alpha)^{20}_D$ +6.44° (C=0.87, MeOH)

EXAMPLE 45

The compound (50) (80 mg, 0.067 mmol) was dissolved in MeOH (5 ml), to which 10% Pd-C (100 mg) was added. Catalytic reduction was carried out at room temperature for 24 hours, filtered to remove Pd-C and concentrated in vacuo to give quantitatively the compound (51) (42 mg).

(The Compound (51))

Rf 0.34 BuOH:EtOH:H2O (4:2:2)
$(\alpha)^{19}_D$ +19.2° (C=1.53, H2O)

EXAMPLE 46

The compound (47) (507 mg, 0.373 mmol) was dissolved in acetic anhydride (5.0 ml) and pyridine (5.0 ml) and stirred at room temperature for 24 hours. The reaction mixture was subjected to silicagel column chromatography (Wakogel C-300, 50 g) and eluted with 10% MeOH-containing toluene to give the compound (52) (484 mg, 93%).

(The Compound (52))

$(\alpha)^{27}_D$ −3.33° (C=1.17, CHCl3)
Analysis: Calcd.: C, 65.27; H, 6.27; N, 1.00. (for C76H87NO24) Found: C, 65.25; H, 6.47; N, 1.03.
PMR 400MHz CDCl3 ppm (TMS) 1.762, 1.855, 1.973, 2.000, 2.013, 2.073, s, CH3CO, 2.598, q, J=12.69, 4,64, H-3c, eq, 3.834, OCH3, s

EXAMPLE 47

The compound (52) was dissolved in MeOH (15 ml), to which 10% Pd-C (200 mg) was added. Catalytic reduction was carried out. After the reduction was completed, the reaction mixture which contained the compound (53) (TLC, BuOH-EtOH-H2O 4:2:2, Rf 0.55) was filtered to remove Pd-C and concentrated in vacuo. The residue was dissolved in acetic anhydride (5 ml) and pyridine (5 ml) and stirred at room temperature for 2 hours. The mixture was concentrated in vacuo. The residue was subjected to silicagel column chromatography (C-300, 10 g) and eluted with ethyl acetate to give the compound (54) (235 mg, 69.3%).

(The Compound (54))

Rf 0.28 (EtOAc)
Analysis: Calcd.: C, 49.77; H, 5.72; N, 1.26. (for C46H63NO30) Found: C, 49.85; H, 5.77; N, 1.45.
PMR 400MHz CDCl3 ppm (TMS) 1.68, t, J=12.45, H-3c, ax, 1.86~2.25, CH3CO, 36H, 2.58, m, H-3c, eq, 3.84, 3.85, s, OCH3

EXAMPLE 48

The compound (54) (190 mg, 0.171 mmol) was dissolved in DMF (1.0 ml) and heated to 50° C., to which hydrazinium acetate (19 mg) was added and stirred for 5 minutes. After cooled, there was added ethyl acetate (10 ml) to the reaction mixture and stirred for 30 minutes. The mixture was diluted with ethyl acetate and washed with saturated NaCl solution. The organic layer was dried on MgSO4 and concentrated in vacuo. The residue was subjected to silicagel column chromatography (Wakogel C-300, 10 g) and eluted with 1% MeOH-containing ethyl acetate to give the compound (19) (148 mg, 81.0%).

(The Compound (19))

Rf 0.29 1% MeOH-containing ethyl acetate
Analysis: Calcd.: C, 49.48; H, 5.76; N, 1.31. (for C44H61NO29) Found: C, 49.25; H, 5.81; N, 1.56.

EXAMPLE 49

The compound (19) (145 mg, 0.136 mmol) was dissolved in methylene chloride (1.0 ml). To this, there was added trichloroacetonitrile (54 μ l) and NaH (60% in oil) (7.0 mg) under ice-cooled condition and stirred for 2 hours. The mixture was concentrated in vacuo. The residue was subjected to silicagel column chromatography (Wakogel C-300, 10 g) and eluted with ethyl acetate to give the compound (20) (110 mg, (The Compound (20))

PMR 400MHz CDCl3 ppm (TMS) 1.68, t, J=12.45, H-3c, ax, 1.86~2.10, CH3COO, 33H, 2.58, q, J=12.69, 4.63, H-3c, eq, 3.848, s, OCH3, 6.49, d, J=3.67 H-la, 8.66, s=NH
CMR 25MHz CDCl3 ppm 93.13, C-la, 96.88, c-2c,

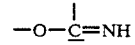

EXAMPLE 50

Activated molecular sieves 4A (0.5 g), the compound (20) (60 mg, 0.049 mmol), and the compound (IV) (37 mg, 0.049 mmol) were dissolved in CHCl3 (0.5 ml) under argon atmosphere and ice-cooled condition. To this mixture, there was added BF3 . Et2O (7 μ l) with stirring. The mixture was stirred at ice-cooled condition for two hours and at room temperature for 24 hours. The reaction mixture was diluted with CHCl3, filtered through Celite. Insolubles were filtered. The filtrate was concentrated in vacuo. The residue was subjected to silicagel column chromatography (Wakogel C-300, 12 g) and eluted with 3% MeOH-containing chloroform to give the compound (21) (32 mg, 36%).

(The Compound (21))

$(\alpha)^{25}_D$ +4.51° (CHCl3, C=1.13)
Rf 0.39 EtOAc
Analysis: Calcd.: C, 61.91; H, 8.16; N, 1.55. (for C93H146N2O32) Found: C, 61.93; H, 8.22; N, 1.58.
PMR 400MHz CDCl3 ppm TMS 0.88, t, J=6.35, —CH3×2, 1.25, —CH2—×32, 1.67, t, J=12.46, H-3c, ax, 1.86~2.22, CH3COO×11, 2.57, q, J=12.69, 4.67, H—3c, eq, 3.84, s, CH3—O—, 7.44, m, 2H, 7.60, m ,1H, 7.99, m, 2H, aromatic proton
CMR 22.5MHz CDCl3, ppm, 96.93, C-2c, 100.56 C-la, 101.05, C-1b.

EXAMPLE 51

The compound (21) (25 mg, 0.014 mmol) was dissolved in methanol (0.5 ml). 1 N-NaOMe (56 μ l) was added and stirred at room temperature for 24 hours. The mixture was concentrated. To the residue, there were added water (0.1 ml), THF (0.5 ml) and MeOH (0.5 ml) and stirred for 5 hours. Amberlist A-15 (Tradename) was added to neutralize the mixture and then filtered. The filtrate was concentrated in vacuo. The residue was recrystallized from MeOH to give the compound (22) (11 mg, 61.7%).

(The Compound (22))

PMR 400MHz Me$_2$SO-d$_6$-D$_2$O (98:2 V/V) TMS, ppm 1.23, s, 64H, —CH$_2$—, 1.89, s, 3H, NHCOC$\underline{H_3}$, 1.92, bs, 2H, H-6', 1.37, H-3c, ax, 2.75, H-3c, eq, 4.16, d, J=7.57, H-1a, 4.19, d, J=7.56, H-1b

What is claimed is:

1. A compound of the formula:

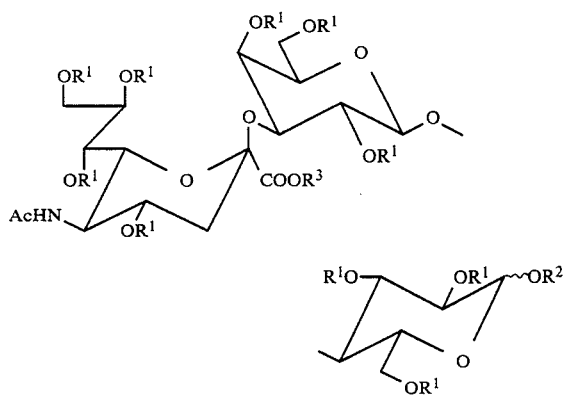

wherein R$^1$ is hydrogen or acetyl, R$^2$ is —C(CCl$_3$)=NH or

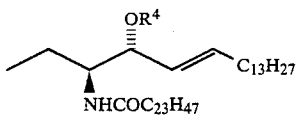

wherein R$^4$ is hydrogen or benzoyl and R$^3$ is hydrogen, alkali metal or methyl.

2. A compound of the formula:

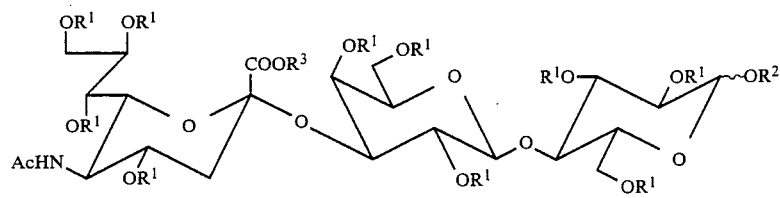

wherein R$^1$ is hydrogen or acetyl, R$^2$ is —C(CCl$_3$)=NH or

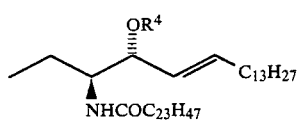

wherein R$^4$ is hydrogen or benzoyl and R$^3$ is hydrogen, alkali metal or methyl, provided that if R$^2$ is

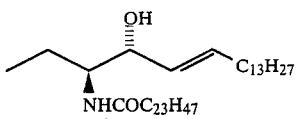

at least one of R$^1$ and R$^3$ is not hydrogen.

3. A compound of the formula:

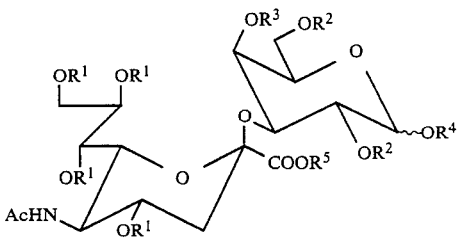

wherein R$^1$ is hydrogen or acetyl, R$^2$ is hydrogen, acetyl or benzyl, R$^3$ is hydrogen, acetyl or benzyl, R$^4$ is hydrogen, benzyl or acetyl and R$^5$ is hydrogen, alkali metal or methyl.

4. A compound of the formula:

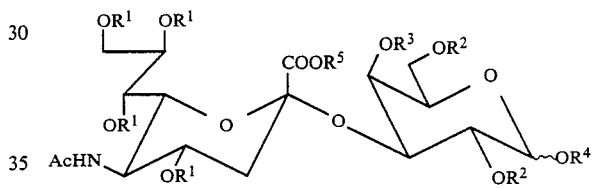

wherein R$^1$ is hydrogen or acetyl, R$^2$ is hydrogen, acetyl or benzyl, R$^3$ is hydrogen, acetyl or benzyl, R$^4$ is hydrogen, benzyl or acetyl and R$^5$ is hydrogen, alkali metal or methyl.

5. A compound of the formula:

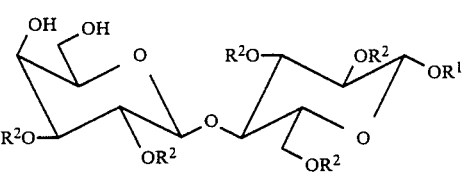

wherein R$^1$ is allyl and R$^2$ is benzyl.

6. A process for the production of a compound of the formula:

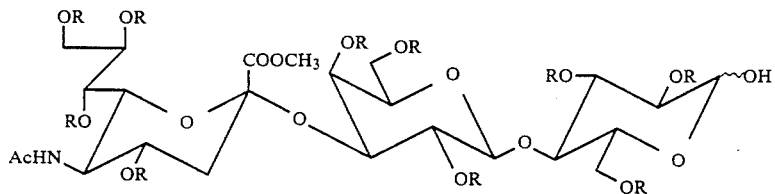

wherein R is acetyl, which comprises treating a compound of the formula:

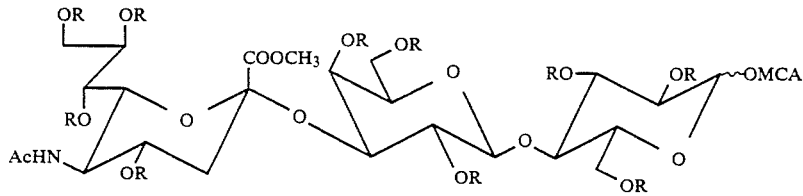

wherein R is acetyl and MCA is monochloroacetyl,

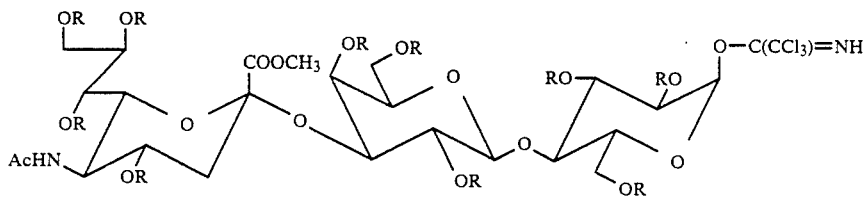

with thiourea and alkali metal acetate.

7. A process for the production of a compound of the formula:

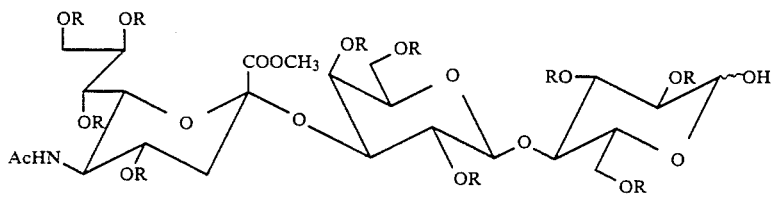

wherein R is acetyl, which comprises treating a compound of the formula:

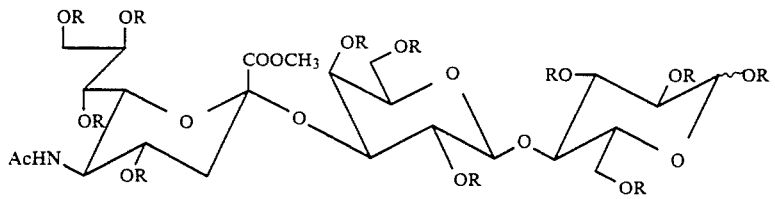

wherein R is acetyl, with hydrazinium acetate at 30° C.

to 80° C. for 5 to 30 minutes in a solvent such as dimethyl formamide.

8. A compound of the formula:

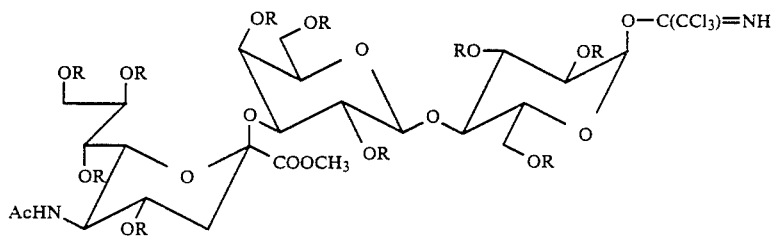

wherein R is acetyl.

9. A compound of the formula:

wherein R is acetyl.

* * * * *